United States Patent [19]
Boyle et al.

[11] Patent Number: 5,654,407
[45] Date of Patent: Aug. 5, 1997

[54] HUMAN ANTI-TNF ANTIBODIES

[75] Inventors: Petra Boyle, Pinole; Gayle D. Wetzel, Martinez; Kenneth J. Lembach, Danville, all of Calif.

[73] Assignee: Bayer Corporation, Berkeley, Calif.

[21] Appl. No.: 435,246

[22] Filed: May 5, 1995

Related U.S. Application Data

[63] Continuation of Ser. No. 145,060, Oct. 29, 1993, abandoned, which is a continuation-in-part of Ser. No. 26,957, Mar. 5, 1993.

[51] Int. Cl.$^6$ ................................................. C07K 16/24
[52] U.S. Cl. ..................... 530/388.15; 424/142.1; 424/145.1; 424/158.1; 435/335; 530/388.23; 530/388.24
[58] Field of Search ............................ 424/142.1, 145.1, 424/158.1; 435/70.21, 172.2, 335; 530/388.15, 388.23, 388.24, 389.2

[56] References Cited

PUBLICATIONS

Rhein, R., "Another Sepsis Drug Down—Immunex' TNF Receptor," *Biotechnology Newswatch* Oct. 4, 1993, McGraw Hill, Publishers., pp. 2–3.

Boyle et al., "A Novel Monoclonal Human IgM Autoantibody Which Binds Recombinant Human and Mouse Tumor Necrosis Factor–α," *Cell. Immunol.* 152:556–568, 1993.

Boyle et al., "The B5 Monoclonal Human Autoantibody Binds to Cell Surface TNFα on Human Lymphoid Cells and Cell Lines and Appears to Recognize a Novel Epitope," *Cell. Immunol.* 152:569–581, 1993.

*Primary Examiner*—Robert D. Budens
*Attorney, Agent, or Firm*—James A. Giblin

[57] ABSTRACT

Human monoclonal antibodies (mAbs) which bind to human TNFα are disclosed. Autoantibodies of both the IgM and IgG isotypes are disclosed. A preferred human monoclonal antibody is known as B5 (F78-1A10-B5 mAb) and it binds to recombinant human TNFα (rhTNFα) in ELISA format with a titer comparable to three high affinity neutralizing mouse mAbs. It also binds to cell surface TNFα and prevents TNFα secretion by human monocyte cell lines.

12 Claims, 11 Drawing Sheets

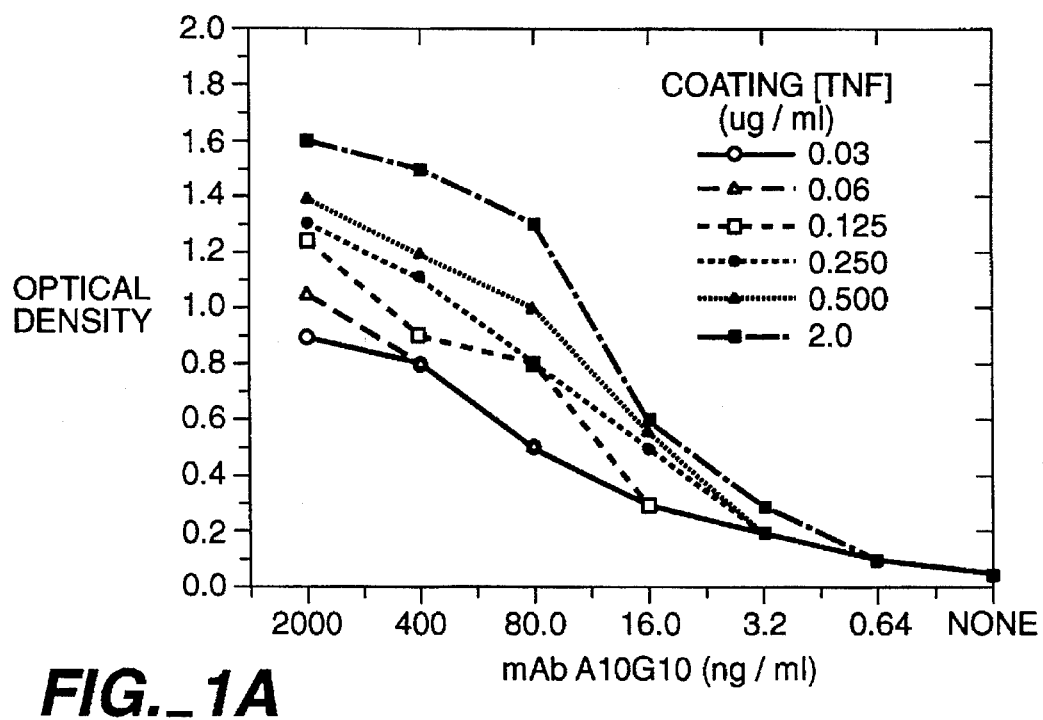
FIG._1A
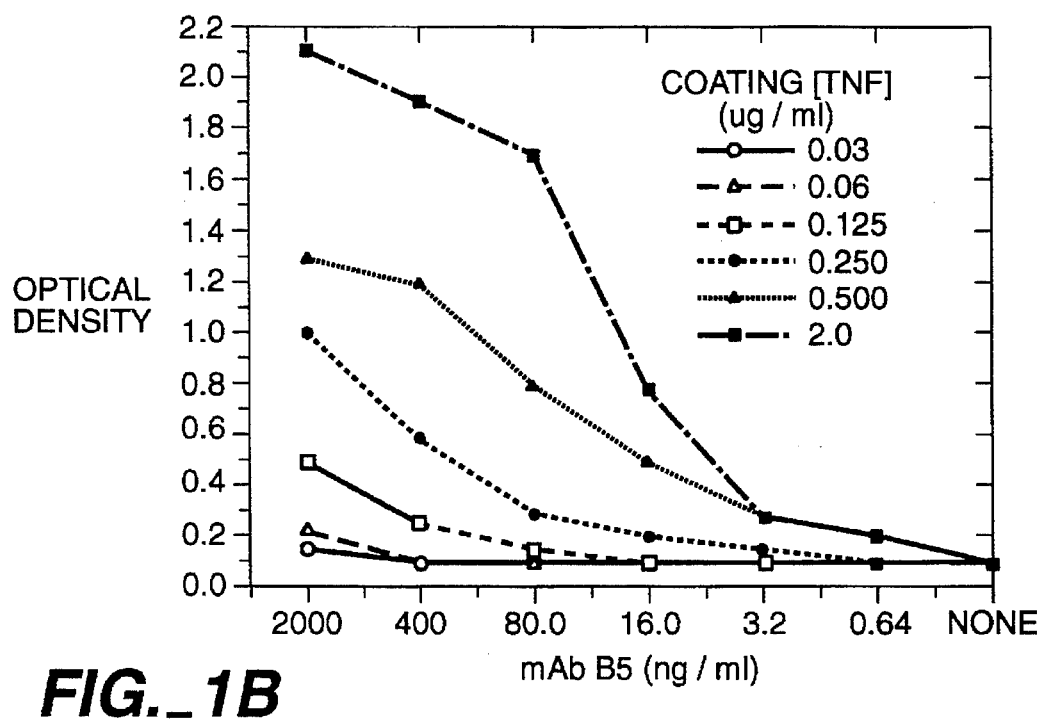
FIG._1B

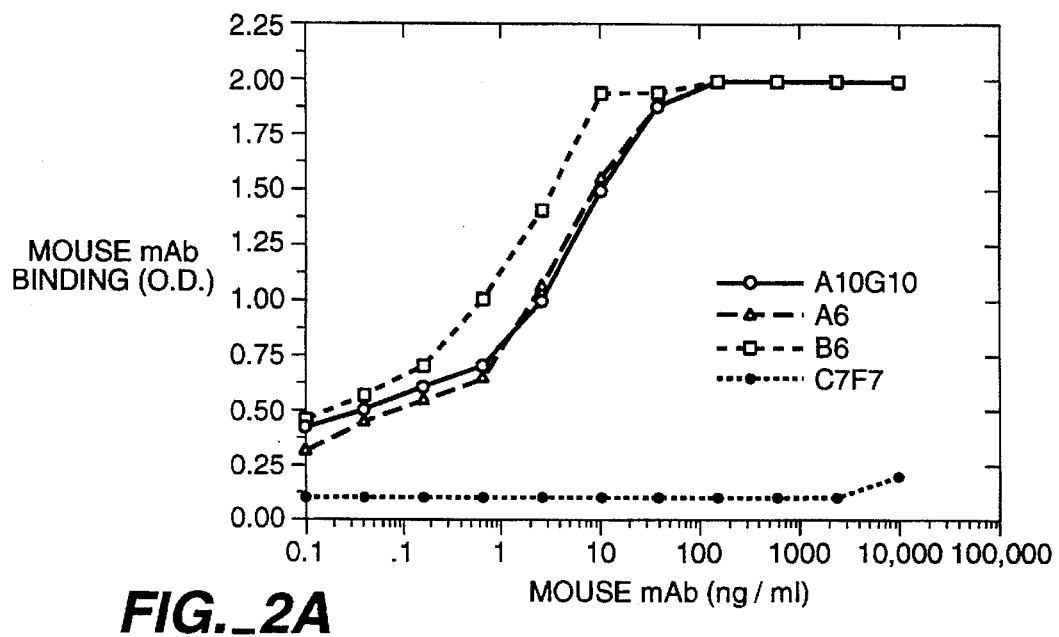
FIG._2A
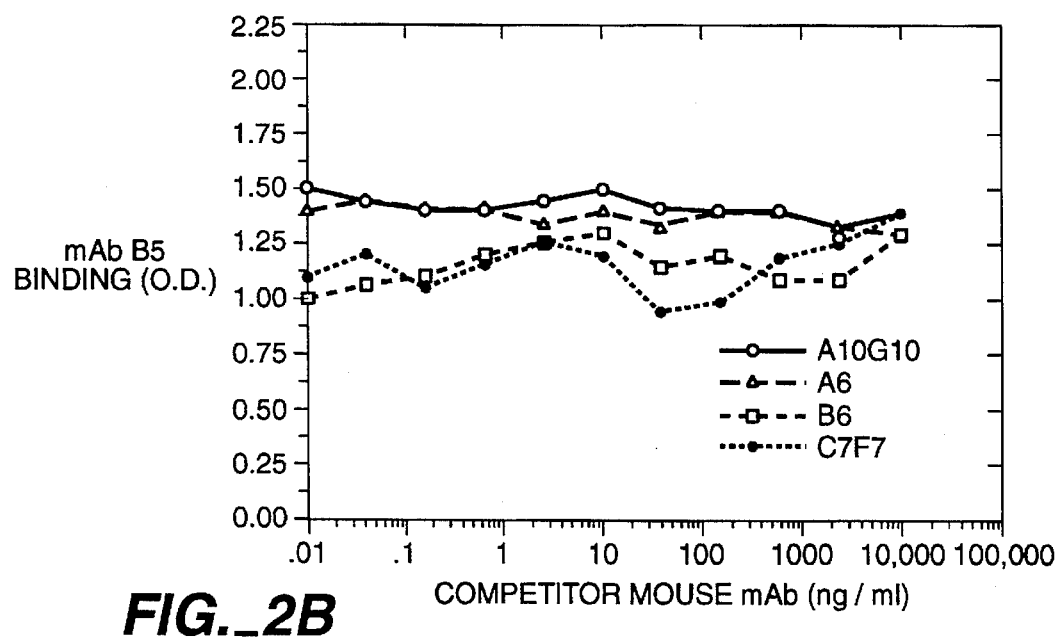
FIG._2B

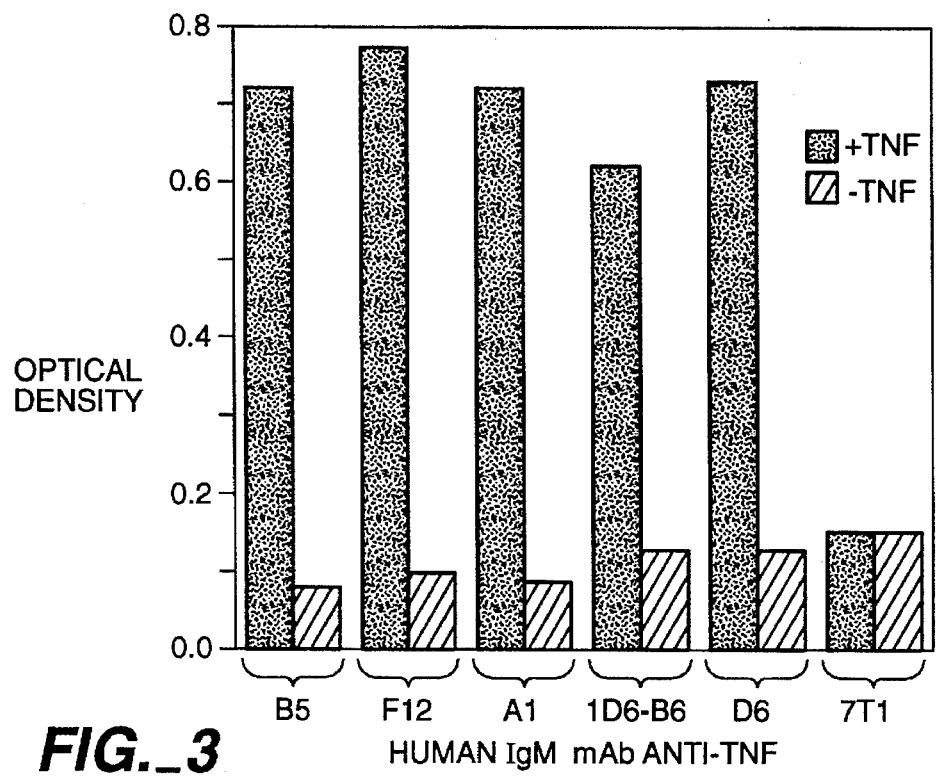
FIG._3
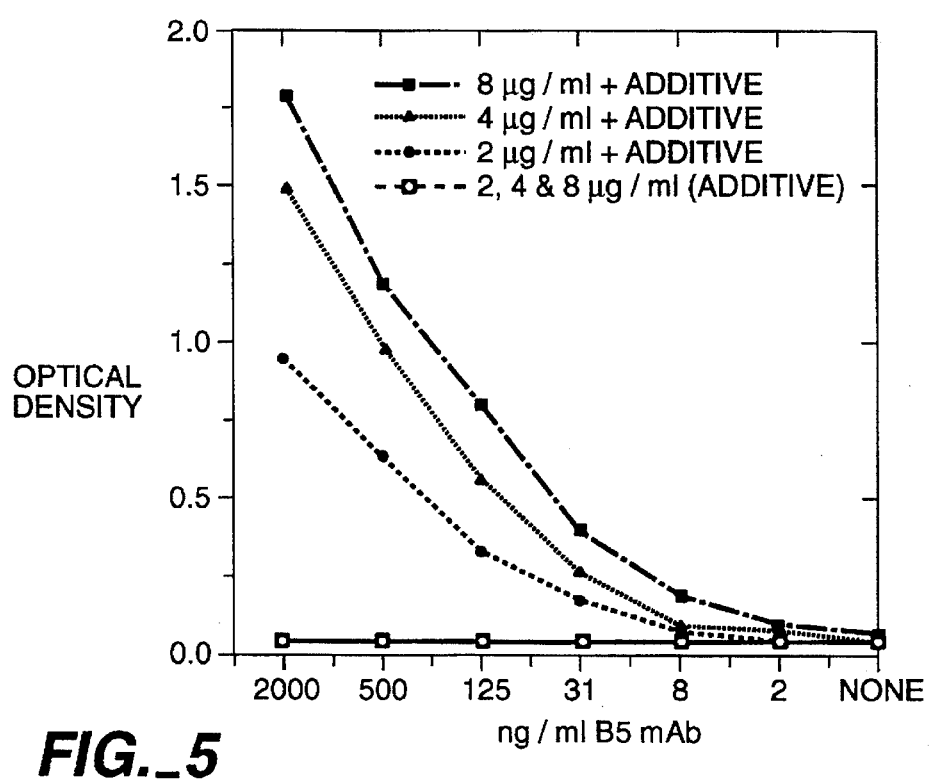
FIG._5

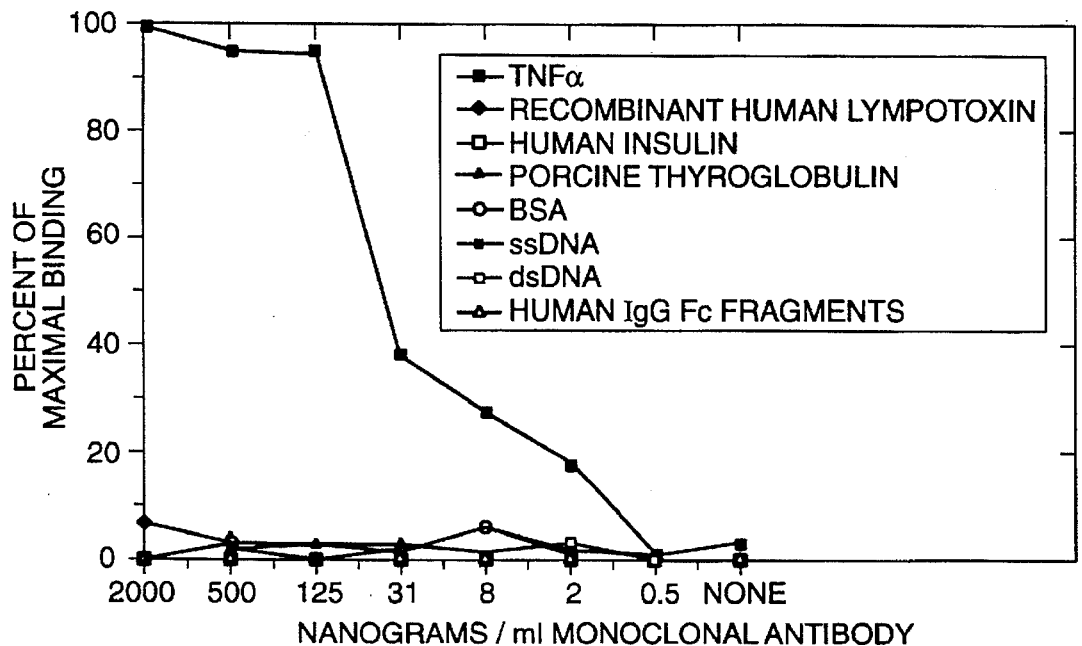
FIG._4A
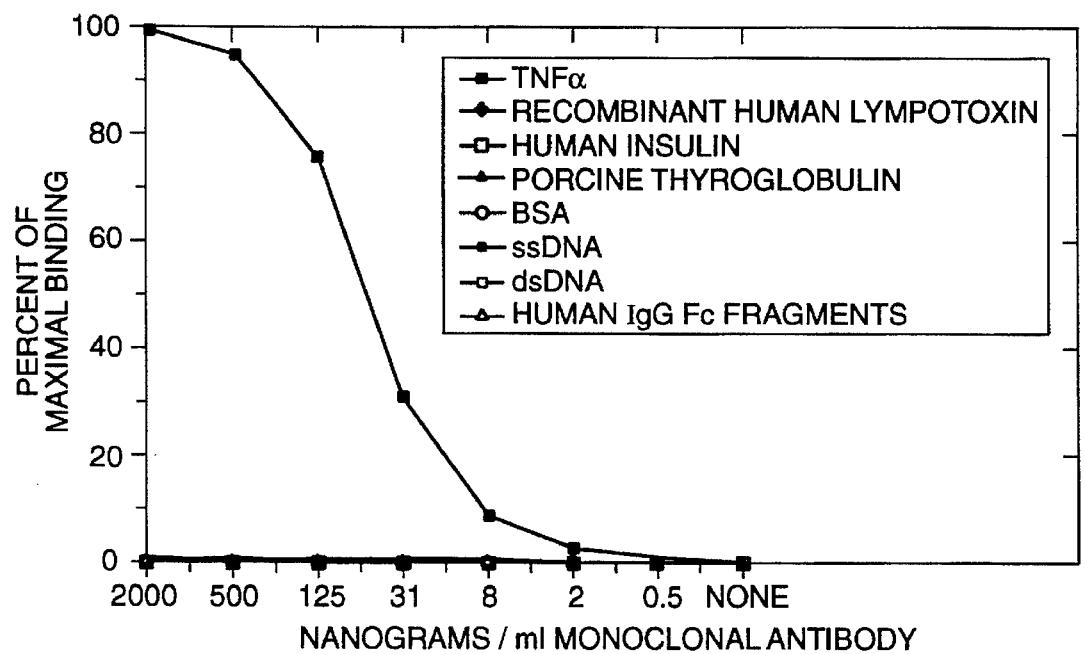
FIG._4B

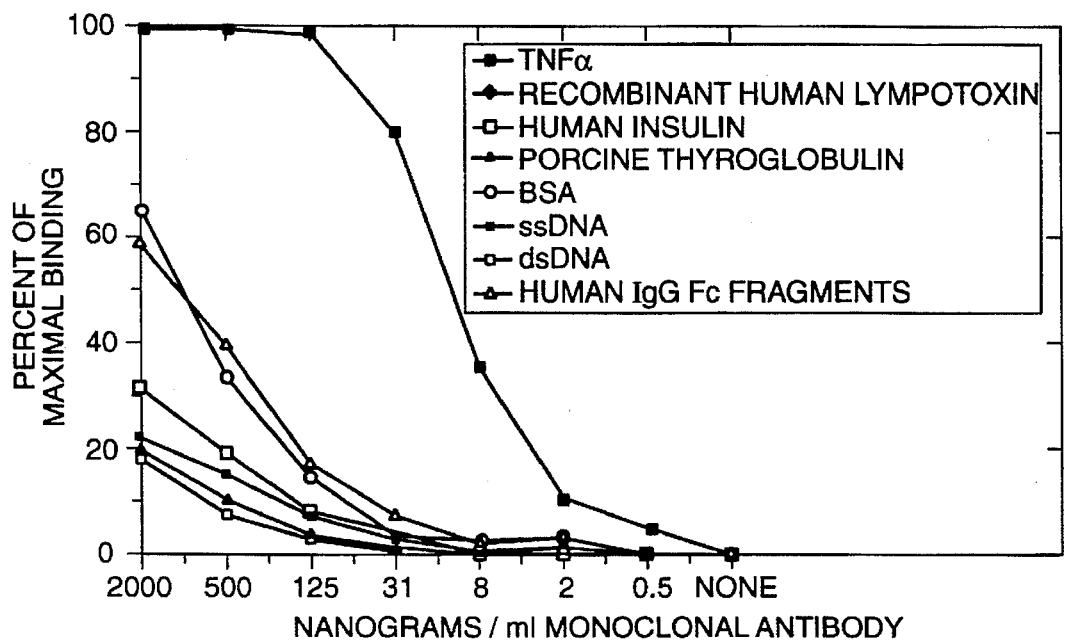
FIG._4C
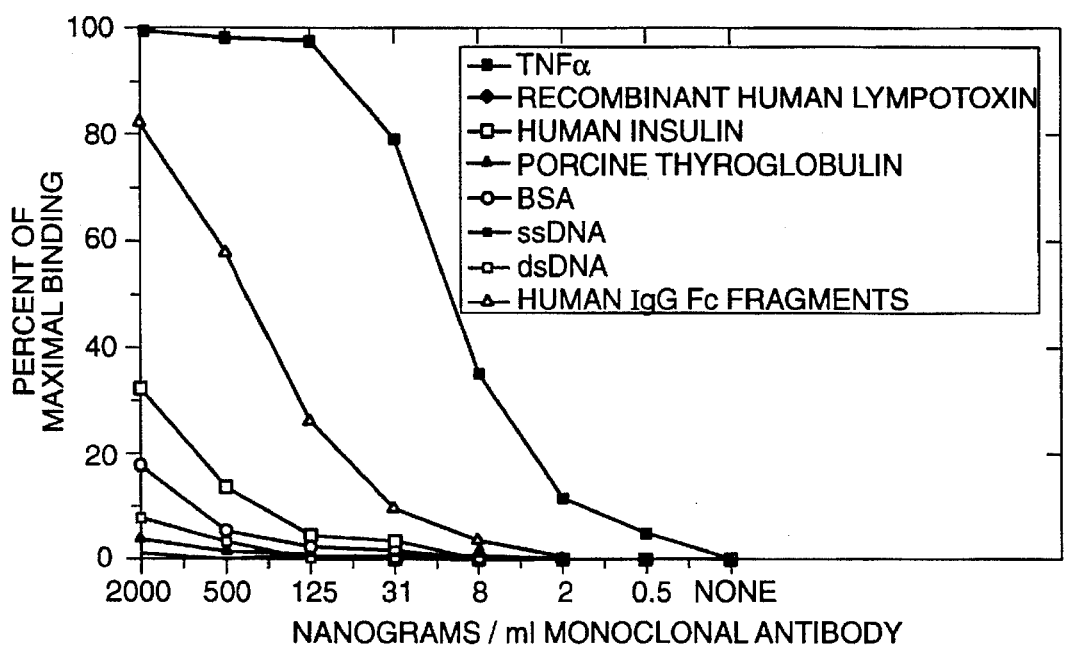
FIG._4D

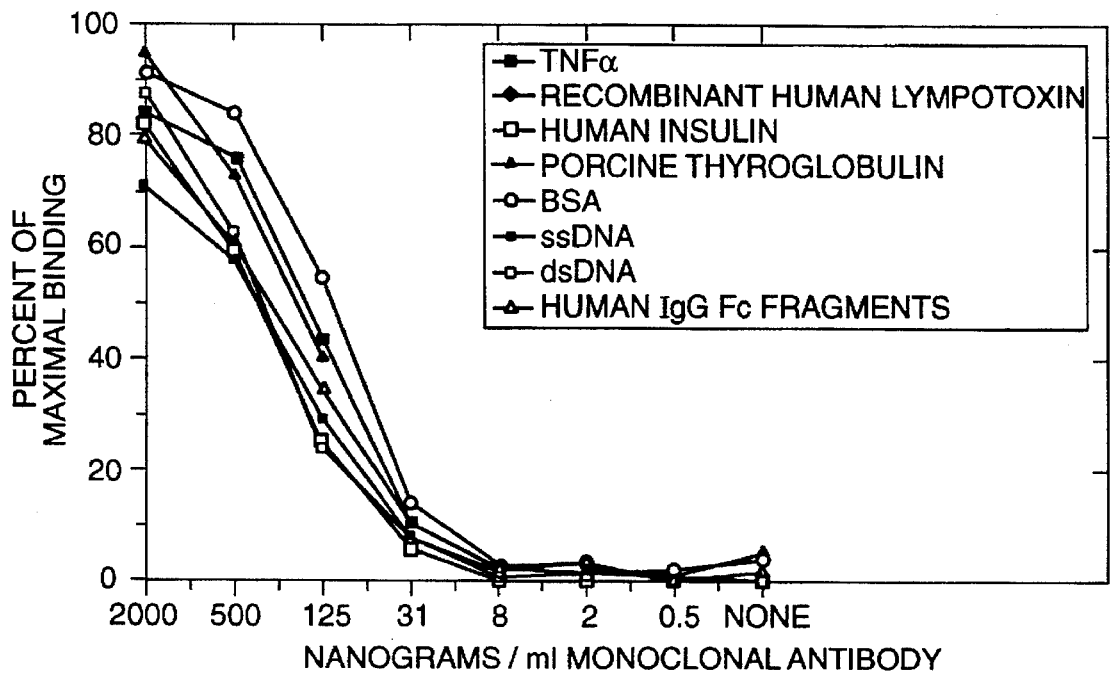
FIG._4E
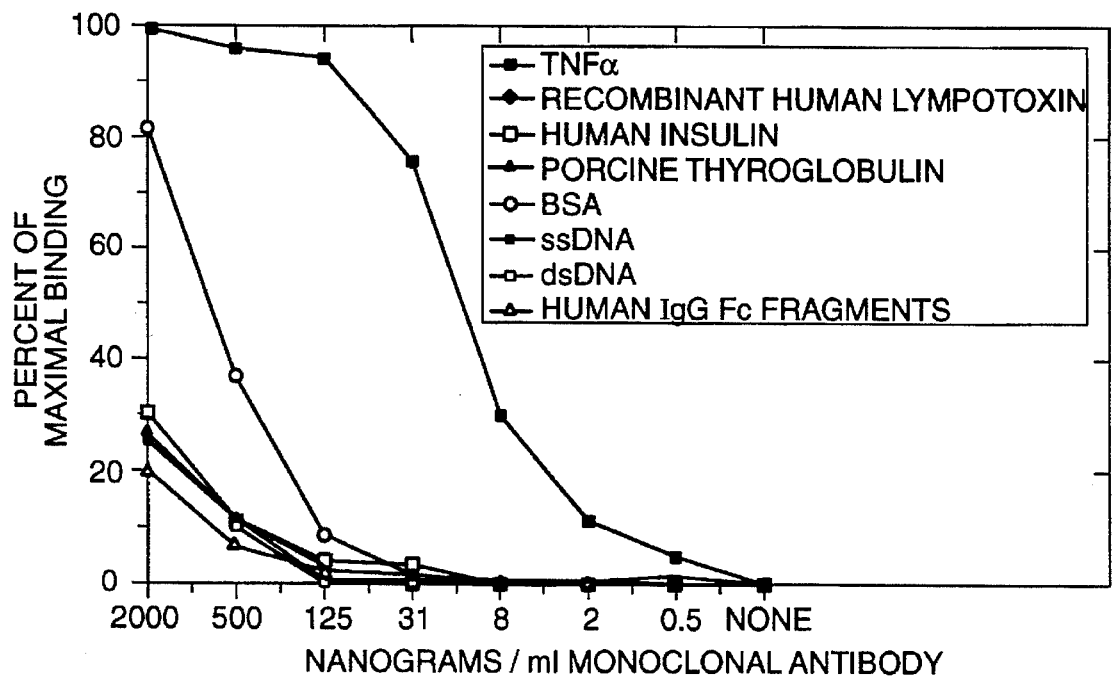
FIG._4F

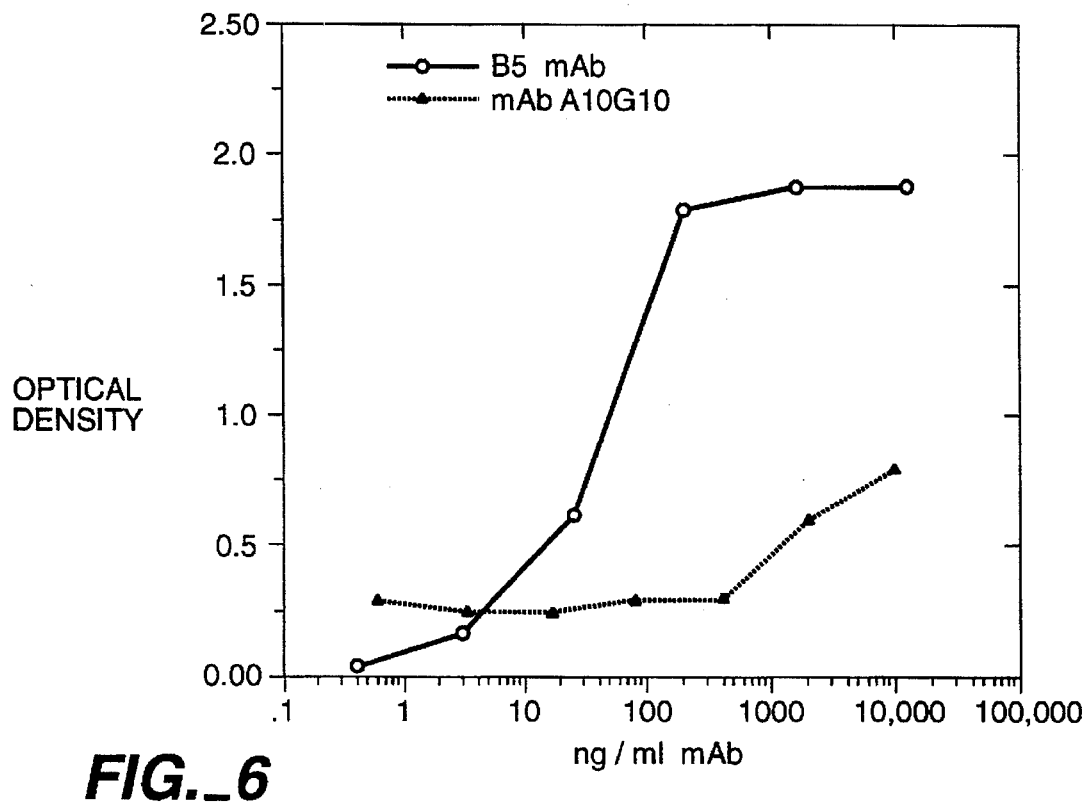
FIG._6
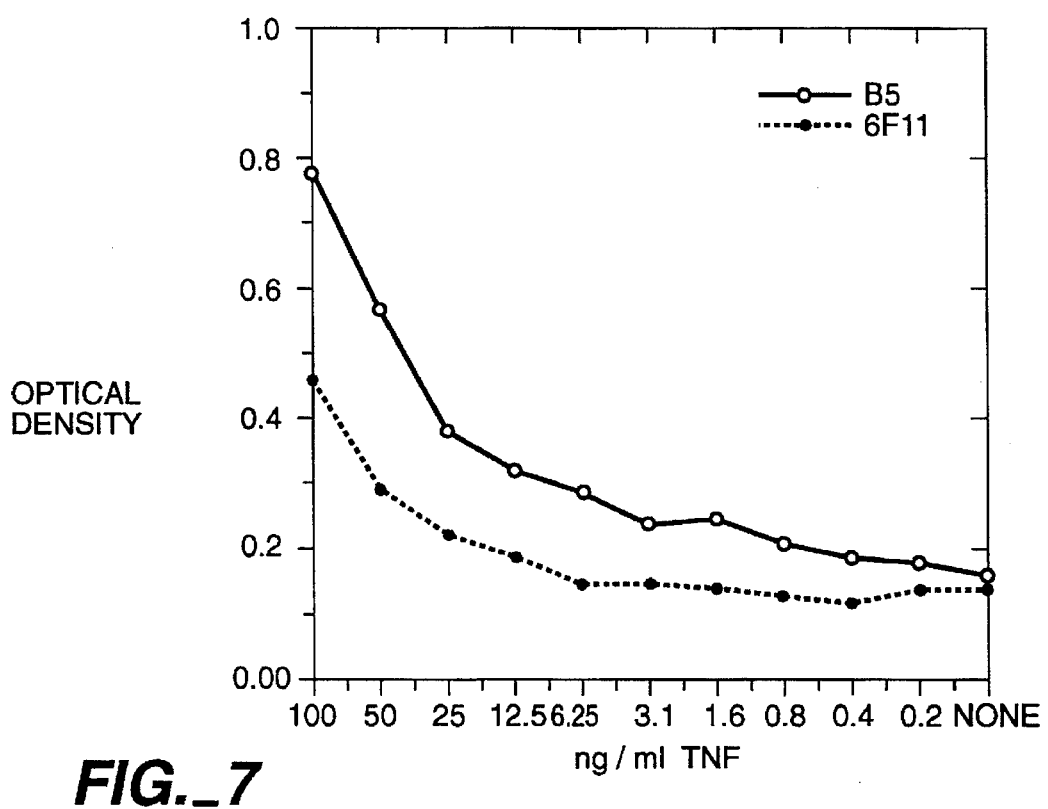
FIG._7

A B C D E F  G H
211 ──
107 ──
69.3 ──
45.8 ──
28.7 ──
18.2 ══
15.4
FIG._8
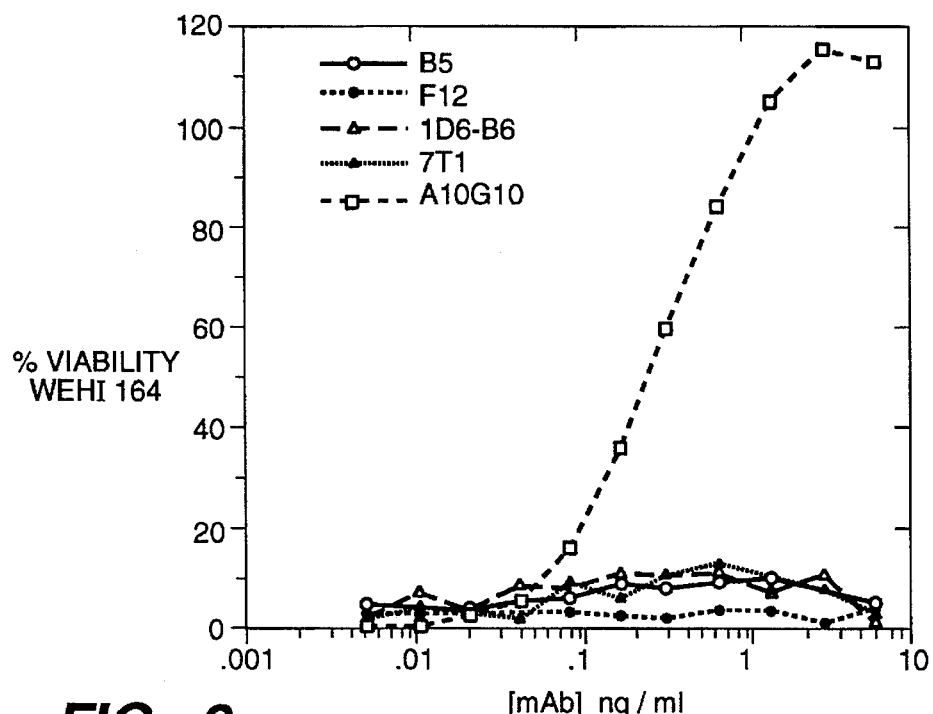
FIG._9

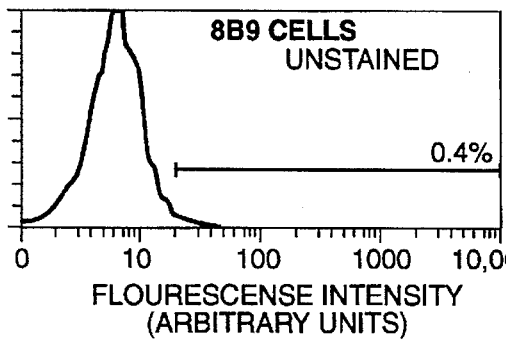
FIG._10A
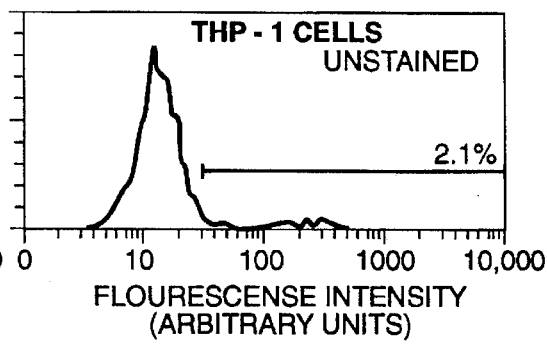
FIG._10B
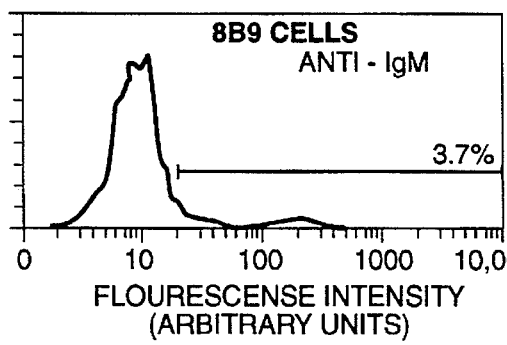
FIG._10C
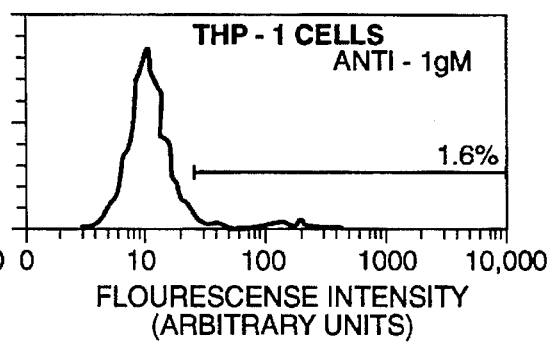
FIG._10D
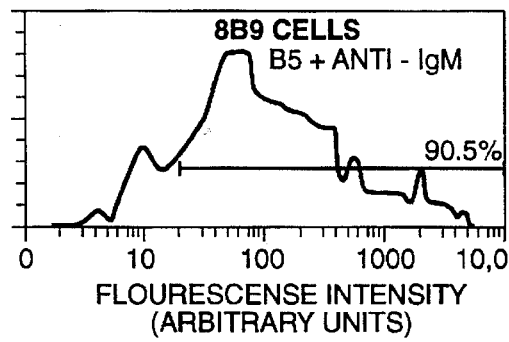
FIG._10E
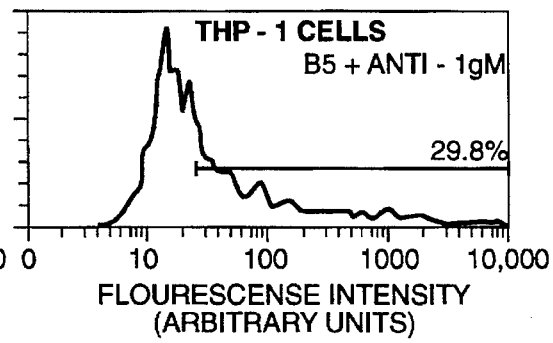
FIG._10F
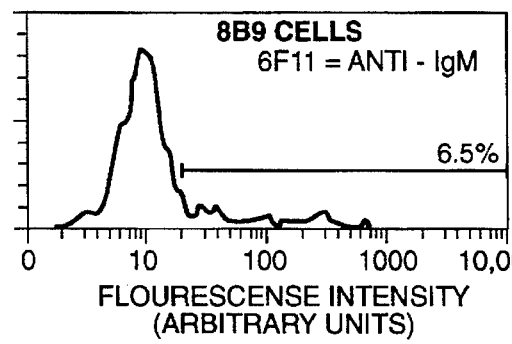
FIG._10G
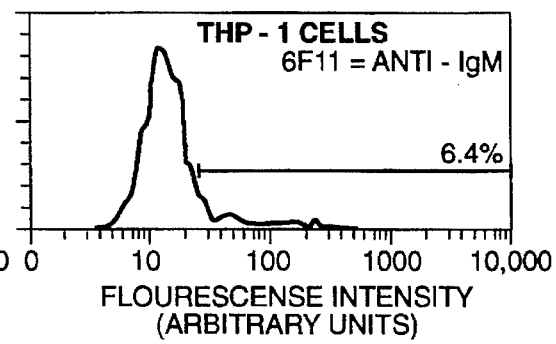
FIG._10H

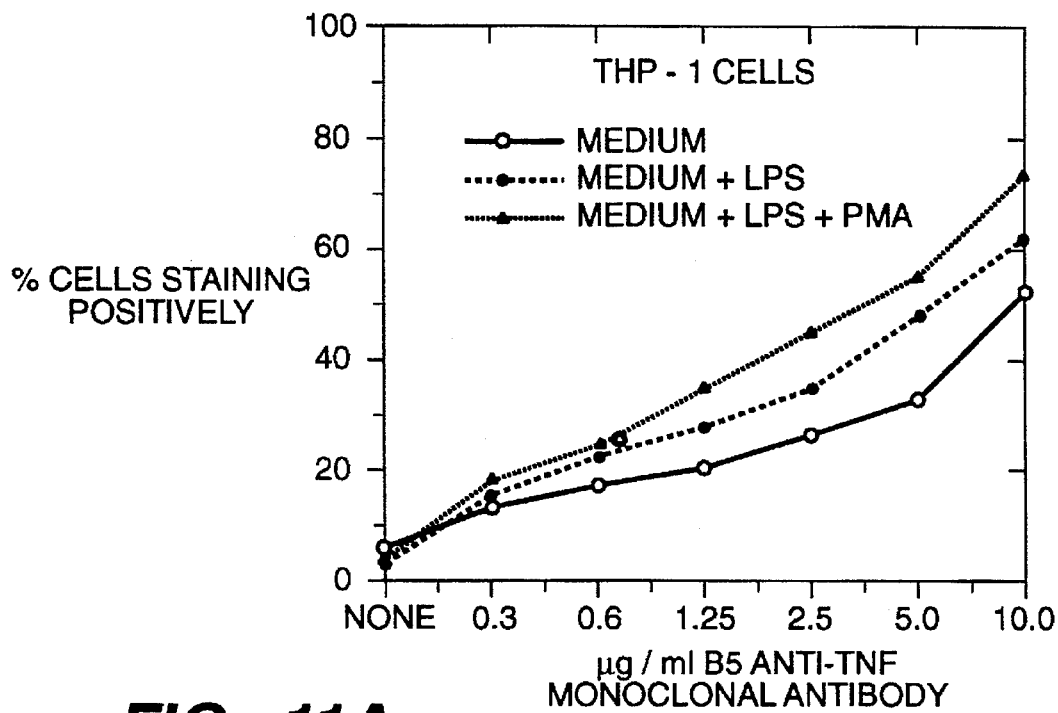
FIG._11A
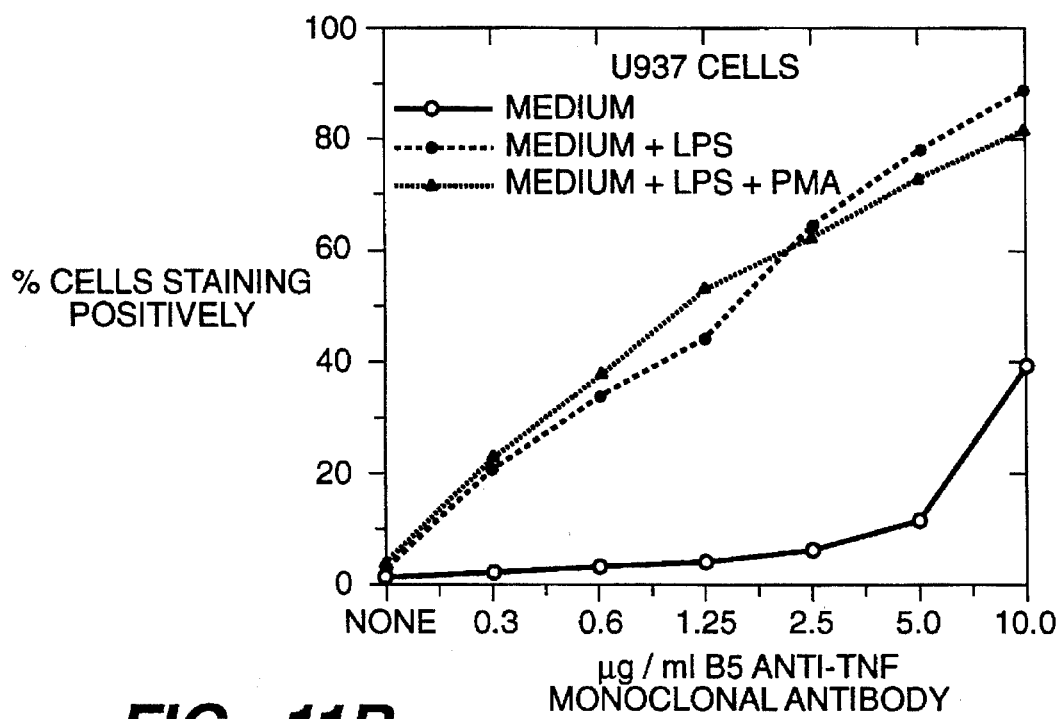
FIG._11B

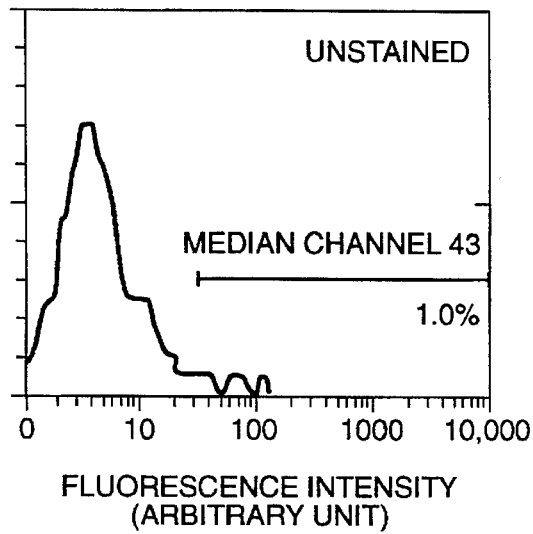
FIG._12A
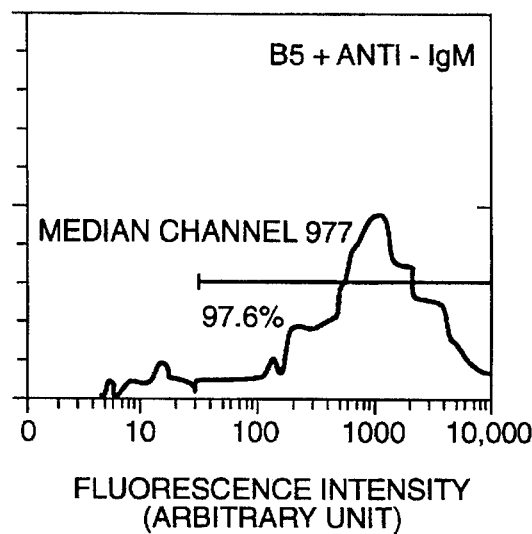
FIG._12B
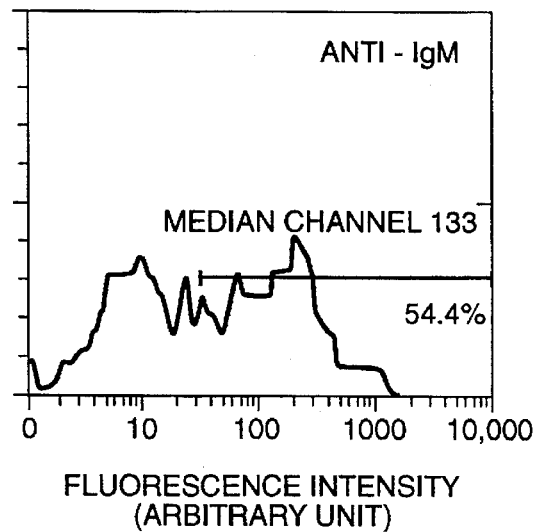
FIG._12C
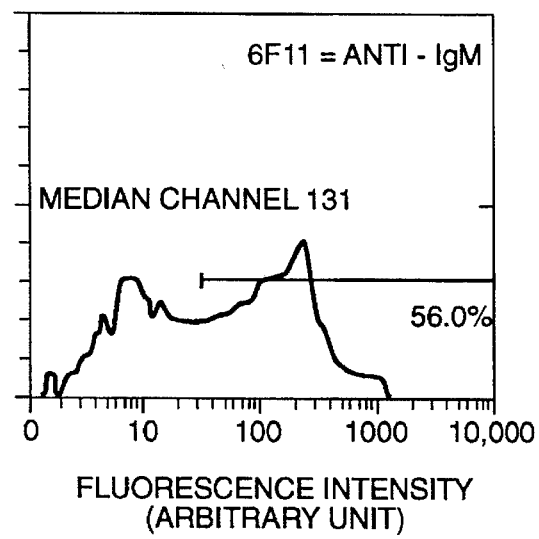
FIG._12D

HUMAN ANTI-TNF ANTIBODIES

CROSS REFERENCE TO RELATED APPLICATIONS

This is continuation of application Ser. No. 08/145,060, filed Oct. 29, 1993, now abandoned, which is a continuation-in-part of application Ser. No. 08/026,957, filed Mar. 5, 1993.

BACKGROUND OF THE INVENTION

1. Field

This disclosure relates generally to monoclonal antibodies and specifically with human antibodies that bind to human tumor necrosis factor (TNFα).

2. Prior Art

TNFα is a pluripotent and pleiotropic cytokine. It is produced principally by activated macrophages, however its synthesis and secretion have also been observed using granulocytes, tonsil B cells, B cell lines, natural killer cells, T cell lines, primary chronic malignant B cell isolates, and peripheral blood T cells.

TNFα can also be expressed on cell surfaces, apparently in two forms. One is a 26 kd molecular weight integral type 2 transmembrane protein on monocytes, T cells and some other cells. The other form is the secreted 17 kd product which is bound to its receptor.

Among the many activities of secreted TNFα are thymocyte growth factor, B cell growth and maturation factor, production in vivo of hemorrhagic necrosis, weight loss, cardiovascular collapse and multiple organ failure. Naturally, these latter activities are the source of the clinical interest in TNFα.

During septic shock, as well as inflammatory diseases, synthesis and secretion of TNFα, IL-1, IL-6 and IL-8 have been documented. Hence the immune systems of some individuals are exposed chronically to these cytokines. Indeed, low affinity antibodies to TNFα have been reported (A. Fomsgaard et al "Auto-antibodies to Tumor Necrosis Factor α in Healthy Humans and Patients with Inflammatory Diseases and Gram-Negative Bacterial Infections." Scand. J. Immunol. 30:219–23, 1989; and, K. Bendtzen et al "Auto-antibodies to IL-1α and TNFα in Normal Individuals and Infectious and Immunoinflammatory Disorders." Prog. Leukocyte. Biol. 10B:447–52, 1990). These anti-TNFα autoantibodies may, however, not be specific (H. -G. Leusch et al "Failure to Demonstrate TNFα Specific Autoantibodies in Human Sera by ELISA and Western Blot." J. Immunol. Meth. 139:145–147, 1991).

One peculiar feature of human serum, as well as sera from other animals, is its content of natural and so-called polyreactive antibodies. These are usually IgM antibodies which bind to various autoantigens with low affinity (A. B. Hartman et al "Organ Reactive Autoantibodies from Non-Immunized Adult Balb/c Mice are Polyreactive and Express Non-Biased Vh Gene Usage." Molec. Immunol. 26:359–70, 1989; and, P. Casali et al "CD5+ B Lymphocytes, Polyreactive Antibodies and the Human B cell Repertoire." Immunol. Today. 10:364–8, 1989). Hence the autoantibody-like reactivity to human TNFα might be expected to be low affinity and probably cross-reactive with several other antigens.

Some high affinity neutralizing antibodies to IL-1α have been reported in normal sera (N. Mae et al "Identification of High-Affinity Anti-IL-1α Autoantibodies in Normal Human Serum as an Interfering Substance in a Sensitive Enzyme-Linked Immunosorbent Assay for IL-1α." Lymphokine Cytokine and Research 10:(1) 61–68, 1991) or patient (H. Suzuki et al "Demonstration of Neutralizing Autoantibodies Against IL-1α in Sera from Patients with Rheumatoid Arthritis." J. Immunol. 145:2140–6, 1990).

Despite these considerations, we are unaware of the disclosure of any monoclonal human antibodies specifically binding to TNFα even though it is thought such antibodies may have significant clinical value. Thus, there has remained a need for monospecific monoclonal antibodies to TNFα.

SUMMARY OF INVENTION

We have made monoclonal human antibodies which bind to both human and mouse TNFα. The antibodies bind to recombinant human TNFα (rhTNFα) with a titer comparable to three high affinity neutralizing mouse mAbs, when tested by ELISA. The antibodies most fully characterized are of the IgM isotype although we also prepared antibodies of the IgG isotype. By competition binding experiments, the antibody appears to bind to epitopes on rhTNFα distinct from those bound by the neutralizing mouse mAbs so far described. Specificity analyses indicate that the human IgM autoantibody binds to both human and mouse recombinant TNFα, but not to other antigens commonly recognized by polyreactive natural IgM autoantibodies. The high level of amino acid identity between the human and mouse TNFα molecules suggest that the antibody is monospecific for a given epitope shared by these two forms of TNFα.

The B5 antibody also binds to cell surface TNFα (cs TNFα) on human T cells, B cells, monocytes, a variety of lymphoid and monocyte lineage cell lines of human origin, as well as astrocytomas, a breast carcinoma, and a melanoma. The antibody also binds to chimpanzee lymphocyte and mouse T lymphoma cell line csTNFα. Binding of the antibody to csTNFα is specific since it can be inhibited by TNFα but not by TNFβ, a neutralizing mouse anti-TNFα mAb, nor by a recombinant form of the extracellular domain of the p55 TNF receptor (TNFR). The B5 autoantibody can inhibit LPS induced TNFα secretion by cells of the human monocyte-like cell line THP-1.

Several monoclonal mouse anti-human TNFα antibodies have been described in the literature. None, however, also bind to mouse TNFα.

The specificity, the autoantibody nature, the binding to cell surface TNFα and the ability to inhibit TNFα secretion make B5 a novel mAb.

Characterization of the antibodies and how to make them are described below.

BRIEF DESCRIPTION OF THE FIGURES

FIGS. 1A and 1B show, in graph format, a comparison of solid phase ELISA format binding to rhTNFα of the B5 (human) and A10G10 (murine) monoclonal antibodies. ELISA plates were coated with various concentrations of TNF and titrated doses of mAb were then allowed to bind. Shown are the binding curves for each antibody for the various TNF coating concentrations.

FIGS. 2A and 2B show, in graph format, the lack of competition for binding to TNFα between mouse mAbs and B5 mAb. FIG. 2A shows the binding of three mouse anti-TNF mAbs and the control C7F7 anti-rFVIII mAb binding to solid phase rhTNFα. FIG. 2B shows the lack of inhibition of B5 binding to plate bound TNF when the mouse monoclonals are first allowed to bind to TNF plates and B5 antibody is added subsequently.

FIG. 3 shows, in bar graph format, the binding of human IgM anti-TNF mAbs to rhTNFα captured and presented as a complex by the combination of plate bound mouse mAbs A10G10, B6 and A6. ELISA plates were precoated with the three mouse mAbs and then incubated with rhTNFα. Plates were washed and 20 ug/ml of the indicated human IgM mAbs were then allowed to bind. Solid bars show the binding of the human IgM mAbs to the three mouse mAbs which had been incubated with TNF, the hatched bars show binding of the IgM mAbs when the attached mouse mAbs had not been exposed to TNF.

FIGS. 4A-4F show, in multiple graph format, results of an analysis of the binding specificity of several monoclonal antibodies. Plates where precoated with either recombinant human TNFα (■), recombinant human lymphotoxin (♦), human insulin (□), porcine thyroglobulin (▲), BSA (○), ssDNA (■), dsDNA (□) or human IgG Fc fragments (△). Mouse mAb A10G10 is shown in panel A. Human IgM mAbs B5, 7T1, H5, 1A6B5F and F2.2.34 are shown in panels B, C, D, E and F, respectively. Antibody binding was assessed by ELISA.

FIG. 5 shows, in graph format, binding of B5 to recombinant mouse TNFα. Plastic plates were precoated with a neutralizing monoclonal hamster anti-mouse TNFα antibody at 8 ug/ml (squares), 4 ug/ml (triangles) and 2 ug/ml (circles). Recombinant mouse TNFα was then added at 2 ug/ml (filled symbols) or was not added (open symbols). Human mAb B5 was then allowed to bind at the concentrations indicated. Binding was then assessed by ELISA using anti-human IgM antibody.

FIG. 6 shows, in graph format, a comparison of B5 mAb (triangles) and mAb A10G10 (circles) binding to soluble rhTNFα. Antibodies were bound to plastic plates precoated with anti-human or anti-mouse antibody. Biotinylated TNF was then incubated with the antibodies. Binding of soluble TNFα was detected by enzyme-avidin conjugates.

FIG. 7 shows, in graph format, that captured B5 mAb binds soluble TNFα and weakly presents it to A10G10 mAb. B5 mAb anti-TNFα or 6F11 (human anti-LPS IgM) as a control, were allowed to bind to plates precoated with anti-human IgM. Soluble TNFα was then allowed to bind to the complexed human mAbs. Mouse mAb A10G10 was added and its binding to TNF complexed to B5 mAb was detected by enzyme linked anti-mouse IgG antibody.

FIG. 8 shows, in photograph format of Western blots, the binding of several human IgM antibodies to mouse TNFα and binding of the human B5 mAb to human TNFα. Recombinant mouse TNFα (lanes A–G) and rhuTNFα (lanes H and I) were electrophoresed under reducing conditions and transferred to nitrocellulose. Mouse TNFα was blotted with the following monoclonal antibodies: 7T1 (lane A), B5 (lane B), 1A6B5F (lane C), 6F11 (lane D), H5 (lane E), A8 (lane F), and no primary antibody (lane G). Human TNFα was electrophoresed in lanes H and I. Lane H was then blotted with B5 mAb and lane I with 6F11 mAb. Lanes A–F, H and I were then exposed to biotinylated anti-human IgM. Lane F was exposed to biotinylated anti-human IgG, since A8 is an IgG antibody. All lanes were then exposed to the developing reagent avidin coupled horse radish peroxidase. Molecular weight standards, ranging in molecular weight from 211 kd to 15.4 kd, were run in parallel and their positions are indicated.

FIG. 9 shows, in graph format, the neutralization of rhTNFα by A10G10 mouse mAb and lack of neutralization by human mAbs. WEHI 164 cells were incubated with a cytotoxic dose of rhTNFα in the presence of titrated concentrations of mAb. Viability was subsequently assessed.

FIGS. 10A-10H show, in histogram format, the fluorescence staining profiles of two cell lines stained with human IgM anti-TNFα mAbs. 8B9 cells (FIG. 10A, 10C, 10E, 10G) and THP-1 cells (FIG. 10B, 10D, 10F, 10H) were stained with no antibodies (FIGS. 10A, 10B), with FL-F(ab)'$_2$ anti-human IgM (FIGS. 10C, 10D), B5 IgM anti-TNFα+FL-anti-IgM (FIGS. 10E, 10F) and 6F11 anti-LPS+FL-anti-IgM (FIGS. 10G, 10H). Fluorescence intensity channel numbers, in arbitrary units are plotted against the cells per channel on the ordinate. For each sample 5000 cells were accumulated. The percentages of cells falling within the indicated markers, scored as fluorescence positive, are given.

FIGS. 11A-11B show, in graph format, the detection of cell surface expression of TNFα on THP-1 and U937 cells with the B5 anti-TNFα mAb, and increase in expression with LPS and PMA. THP-1 (FIG. 11A) and U937 (FIG. 11B) cells were incubated 3 hours with medium (open circles), LPS (filled circles) or LPS+PMA (filled triangles).

FIGS. 12A-12D show, in graph format, the shift in staining intensity when B5 anti-TNFα IgM mAb binds to cells being stained with F1-anti-IgM antibody. CD19 positive splenocytes are shown. These were stained with phycoerythrin conjugated anti-CD19 and only positive cells were further analyzed for fluorescein conjugated antibody staining. FIG. 12A shows C19+ splenocytes not stained with FL-anti-IgM. FIG. 12B shows staining of these cells with B5+FL-anti-IgM, FIG. 12C shows staining with FL-anti-hIgM alone, and FIG. 12D shows staining with control 6F11 anti-LPS IgM+FL-anti-IgM. The percentages of cells within the indicated markers are given, indicating the percentage of cells staining positively with the fluorescein conjugated antibody. The median channel numbers for the positive populations are also given. These numbers reflect the staining intensity, measured in arbitrary units, for the florescence positive populations.

DETAILED DESCRIPTION OF INVENTION

Materials and Methods

Reagents

Bayer A. G., Wuppertal, Germany provided rhTNFα. The rmTNFα and rhLT were purchased from Genzyme. Human IgG Fc fragments were purchased from Chemicon. Insulin was purchased from Novo Nordisk Labs and all the other antigens used in ELISAs were purchased from Sigma. The Staph. aureus Cowan strain was purchased from Calbiochem (San Diego, Calif.). The anti-human IgD-Dextran conjugate was obtained from a private source. Phorbol myristic acid, mouse IgG$_1$, staphylococcal enterotoxin B (SEB) and phytohemagglutinin (PHA) were purchased from Sigma. E. coli LPS was obtained from a private source. The different fetal bovine sera (FBS) were purchased from Hyclone.

The cell lines mentioned in Table 2 were all purchased from the American Type Culture Collection (ATCC), except for the 8B9 EBV transformed human B cell line which was obtained from Genetic Systems Corporation. The American Type Culture Collection (ATCC) is located at 12301 Parklawn Drive, Rockville, Md. 20852.

TNF was biotinylated using standard techniques; briefly, N-hydroxysuccinimidyl ester of biotin was added to TNF dissolved in 50 mM NaHCO$_3$, pH 8.5 for 15 min, quenched with NH$_4$Cl then dialyzed to remove unreacted biotin.

The mouse A10G10 anti-TNFα IgG$_1$ mAb was generated in collaboration with Chiron Corporation and has an ATCC designation number HB 9736, identified as hybridoma cell line 2-2-3E3.

The A6 and B6 mouse IgG₁ mAb were generated from mice hyperimmunized in our laboratory. All three mouse mAbs neutralize TNF cytotoxicity and have been described in Galloway et al "Monoclonal anti-Tumor Necrosis Factor (TNF) Antibodies Protect Mouse and Human Cells from TNF cytotoxicity." J. Immunol. Meth. 140:37–43, (1991) which is incorporated herein by reference. These mAbs were purified by affinity chromatography.

The polyreactive IgM mAbs 1A6B5F and F2.2.34 were produced and characterized by Kasaian et al "Identification and Analysis of a Novel Human Surface CD5– B Lymphocyte Subset Producing Natural Antibodies." J. Immunol. 148:2690–702 (1992). The 7T1 human IgM mAb was produced and provided in ascites by a private source.

The 6F11-E4 (6F11) EBV transformed B cell lymphoblastoid line having ATCC designation number CRL 1869, produces a human anti-Fisher type 2 Pseudomonas LPS specific IgM antibody and was purchased from Genetic Systems Corporation. The monoclonal antibody from this cell line was produced in our laboratory. It serves as an isotype matched control mAb for the human anti-rhTNFα mAbs. The C7F7 mAb is a mouse IgG₁ anti-hFVIII developed in collaboration with Genentech Inc. and is used as a isotype matched control mAb for the mouse anti-rhTNFα mAbs.

Goat anti-mouse IgG and biotinylated goat anti-human IgG were purchased from Jackson Labs. Biotinylated goat anti-mouse IgG and biotinylated mouse anti-human IgM were purchased from Zymed. Avidin coupled HRP and avidin coupled alkaline phosphatase were purchased from Zymed.

Phycoerythrin conjugated anti-CD3 and anti-CD19 antibodies were purchased from Dakopatts. Phycoerythrin conjugated anti-LeuM3 was purchased from Becton Dickinson. Fluorescein (FL) conjugated F(ab)'₂ anti-human IgM, FL-F(ab)'₂ anti-human IgG and FL-F(ab)'₂ anti-mouse IgG antibodies were purchased from Cappel.

ELISAs

Antigens or capture antibodies (anti-immunoglobulin antibodies) were coated to plastic plates in carbonate/bicarbonate buffer, or PBS containing 20 ug/ml BSA, overnight at 4° C. or 3 hrs at 37° C. Secondary incubations were carried out overnight at 4° C. or at room temperature for a period of 2 hrs or less. Secondary antibodies were biotinylated and their binding was revealed using avidin coupled HRP and avidin coupled alkaline phosphatase.

SPECIFIC EMBODIMENTS

Hybridoma Production

The human IgM mAbs were produced by fusion with the mouse P3X63Ag8.653 non-secreting myeloma. Peripheral blood mononuclear cells from a CMV positive donor were separated by centrifugation on Ficoll, treated with L-leucyl leucine methyl ester, incubated in vitro with antigen and subsequently transformed with EBV. Transformants were distributed at limiting concentrations and cells producing antibody binding to TNF were fused and subsequently subcloned. The B5 hybridoma was subcloned a minimum of 5 times and was deposited with ATCC on Mar. 24, 1993, as deposit CRL 11306. The H5 and 7T1 mAbs were produced by fusion of human tonsillar cells immunized in vitro. Monoclonal human IgM antibodies were affinity purified by standard techniques for use in subsequent experiments.

Cytotoxicity Assay

To assess the TNF neutralizing ability of various mAbs, the assay described by Galloway et al (cited above) was used with the following minor modifications. Briefly, 20 pg/ml TNF were incubated overnight with 60,000 WEHI 164 cells and the test mAb. Viable cells were then detected by crystal violet staining and reading optical density at 570 nm.

Western Blotting

Recombinant huTNFα (100 ug/ml plus 100 ug/ml BSA) and recombinant mTNFα (5 ug/ml with 100 ug/ml BSA) were electrophoresed in the presence of βmercaptoethanol and SDS on 12% polyacrylamide gels. Proteins were then electro-transferred to nitrocellulose which was then blocked with BSA. Test mAbs were allowed to bind and were subsequently detected with biotinylated anti-immunoglobulin reagents. Streptavidin-HRP was then added followed by substrate.

Fluorescence Analyses

One million cells were stained with optimal concentrations of primary antibody, usually 2.5–40 ug/ml at 4° C. for ½ hour in PBS containing 1% FBS and 0.02% sodium azide. Optimal concentrations of fluorescent secondary antibodies were added, after two cell washes, for a similar time in similar buffer. After washing, cells were fixed with 2% paraformaldehyde solution. Cell fluorescence was then analyzed on a FACSCAN (name of instrument).

Inhibition of LPS stimulation of TNFα Secretion

One million THP-1 cells/ml were incubated 4 hrs with 1 ug/ml E. coli LPS in the presence or absence of 40 ug/ml human IgM antibodies. Supernatants were harvested, centrifuged, filtered and assayed for TNFα cytotoxicity in the WEHI 164 assay mentioned above. Supernatants were titrated and viability was plotted against supernatant dilution. These curves were compared to a standard curve using rhuTNFα to determine the actual concentrations of TNFα produced by the cells.

Results

The monoclonal human IgM antibody B5 binds to solid phase recombinant human TNF (rhTNFα). Several hybridomas secreting monoclonal anti-rhTNFα antibodies have been established in our laboratory. An endpoint titer analysis was performed comparing a panel of 6 human IgM mAbs and 3 human IgG mAbs to three high affinity neutralizing mouse mAbs, A10G10, A6 and B6. ELISA plates were coated with 2 ug/ml rhTNFα. The indicated mAbs were added in titrated concentrations and binding was assessed spectrophotometrically. The minimum mAb concentrations yielding detectable rhTNFα binding are shown. B5 and F12 (F80-1B9-F12) were two of the best human IgM mAbs by this criterion, showing endpoint titers in the subnanogram/ml range. Table 1 presents the data below.

TABLE 1

Comparison of Solid Phase ELISA Format rhTNFα Binding by several Monoclonal Human Antibodies

| mAb | Endpoint Titer (ng/ml) | Ig Class |
| --- | --- | --- |
| A1—G10 | 0.6 | mouse IgG |
| A6 | 0.15 | mouse IgG |
| B6 | 0.08 | mouse IgG |
| F78-1A10-A1 | 0.3 | human igM |
| F78-1A10-B5 | 0.6 | human IgM |
| F80-1B9-F12 (ATCC HB11344) | 0.15 | human IgM |
| F81-4E3-D6 | 9.8 | human IgM |
| F83-1D6-B6 | 625.0 | human IgM |
| D83-1D6-F6 | 1250.0 | human IgM |

TABLE 1-continued

Comparison of Solid Phase ELISA Format
rhTNFα Binding by several Monoclonal Human Antibodies

| mAb | Endpoint Titer (ng/ml) | Ig Class |
| --- | --- | --- |
| F83-1A7-G7 | 0.76 | human IgG |
| F83-1G12-C1 | 1.5 | human IgG |
| F83-4D3-D8 | 0.38 | human IgG |
| F83-8D5-F10 | 0.76 | human IgG |
| F84-6G9-D6 | 1563.0 | human IgG |

ATCC HB 11344 was deposited on May 11, 1993.

It should be noted that the ranges and endpoint titers were similar for the IgM anti-TNFα mAbs and the IgG anti-TNFα mAbs.

FIG. 1 presents a more extensive comparison of the human B5 and mouse A10G10 mAbs. Binding of both mAbs was concentration dependent regardless of TNF coating concentration. The B5 mAb bound slightly better than A10G10 with high TNF coating concentrations. As the TNF coating concentration was reduced, however, the binding of B5 decreased more rapidly than that of A10G10. This is consistent with B5 having a lower affinity than A10G10 for rhTNFα. These data show that the B5 mAb binds to solid-phase rhTNFα.

B5 mAb binds to a different epitope on rhTNFα than those bound by three mouse anti-TNF mAbs. Competitive binding experiments have shown that A10G10 and B6 recognize similar epitopes on rhTNFα whereas A6 recognizes a different epitope (data not shown). To examine the epitope binding specificity of B5, competitive binding experiments were performed using the mouse mAbs and B5.

The mouse mAbs were added at different concentrations to ELISA plates previously coated with TNFα. An optimum concentration of B5 mAb was then added and binding was subsequently detected with biotinylated anti-human IgM. If the mouse mAbs recognize the same epitope as B5 mAb, they should inhibit B5 mAb binding in a concentration dependent manner.

As shown in FIG. 2A, binding of the mouse mAbs to plate bound rhTNFα is concentration dependent. FIG. 2B shows that none of the mouse mAbs interfered with rhTNFα binding by a fixed amount of B5 mAb, even at concentrations of the mouse mAbs significantly in excess of those required for maximal binding to the plate. These data suggest that B5 recognizes an epitope on rhTNFα different from those recognized by A10G10, A6 and B6.

To support this finding, rhTNFα was added to ELISA plates previously coated with the combination of A10G10, B6 plus A6 mAbs. B5 mAb was then added to test whether it could bind to rhTNFα complexed to, or captured by, the mouse mAbs.

FIG. 3 shows that B5 and all the other human IgM mAbs, except 7T1, bound to rhTNFα complexed to mouse mAbs. Binding of the human mAbs was not seen in the absence of rhTNFα, demonstrating specificity for some epitope of rhTNFα. The failure of 7T1 mAb to bind to complexed TNF may be simply due to a low affinity. These results support the conclusion that the human IgM mAbs B5, F12, A1, B6 and D6 and the three mouse mAbs recognize different epitopes on rhTNFα.

B5 mAb is not polyreactive. Since B5 mAb is a human IgM which binds to human TNFα, and therefore has properties which define it as an autoantibody, it was important to determine the quality of this mAb and assess its polyreactivity. We chose a panel of human and non-human antigens typically used to define polyreactivity. Binding of these antigens by B5 mAb, A10G10, two control polyreactive human IgM mAbs 1A6B5F and F2.2.34 and two other human IgM anti-TNF mAbs was compared. The results have been normalized for each antibody to allow direct comparison.

FIG. 4 presents the data from one of four similar experiments. The mouse mAb A10G10 binds specifically to rhTNFα and none of the other antigens. In contrast, the polyreactive mAb 1A6B5F binds to virtually all of the antigens tested. The same was true for the other polyreactive mAb F2.2.34, although binding to BSA and TNF was much stronger than that seen with the other antigens. The B5 mAb showed specificity for rhTNFα. No binding by B5 mAb to recombinant human lymphotoxin (rhTNFβ) nor to any of the other antigens tested was observed. These data provide evidence that the B5 mAb is not polyreactive.

In contrast, the 7T1 and H5 human IgM mAbs bind to human Fc fragments indicating a rheumatoid factor nature. These two antibodies also bind to insulin and 7T1 binds BSA as well. The control polyreactive mAbs appear to define two classes of polyreactivity; one being very broad in specificity and the other being more restricted in the antigens recognized. The 7T1 and H5 mAbs belong to the more restricted class of polyreactive mAbs. The F12 anti-TNF mAb binds to human TNFα but only marginally to other antigens.

B5 mAb binds to recombinant mouse TNFα. During the course of analyzing the specificity of the B5 mAb, we noticed that it also bound to mouse TNFα. To demonstrate this, we first captured mouse TNFα with a neutralizing hamster monoclonal antibody and then allowed B5 to bind to this complex. FIG. 5 shows the results of this kind of experiment. The binding of B5 was dependent on both the concentration of B5 present, and on the concentration of hamster antibody used to coat the plates. No binding was observed when mouse TNFα was not added, indicating the specificity of B5 binding in this system. Other experiments not shown revealed binding to mouse TNFα by the F12 mAb.

B5 mAb binds to soluble rhTNFα with detectable but low affinity. Next, we assessed the mAb's ability to bind to soluble rhTNFα. ELISA plates were coated with anti-human IgM and B5 was then added. The ability of the bound B5 mAb to capture biotinylated rhTNFα was then determined.

FIG. 6 compares the abilities of A10G10 and B5 to bind soluble TNFα under these conditions. Although both mAbs bind soluble rhTNFα, about 300-fold higher concentration of B5 mAb is required for binding equivalent ° 8 to that of A10G10. Furthermore, binding of soluble TNFα to immobilized B5 did not saturate with the concentrations of B5 tested. These results are consistent with a low affinity binding of rhTNFα by B5 mAb. Indeed, attempts to measure the binding constant of B5 mAb revealed an affinity too low to calculate by conventional methods (data not shown).

Soluble rhTNFα binding by B5 was also demonstrated by coating plates with anti-IgM, capturing B5 and then adding unmodified soluble rhTNFα. A10G10 was added next and its binding to this B5-complexed form of rhTNFα was detected with biotinylated anti-mouse IgG. FIG. 7 compares the abilities of B5 and a control human IgM, 6F11, to capture and present soluble rhTNFα to A10G10. Although some non-specific binding was seen with the control mAb, B5 mAb bound approximately four- to eight-fold more rhTNFα in this experiment. These data are consistent with a low binding constant of B5 and add further support for the concept that B5 mAb and A10G10 mAb recognize different epitopes on rhTNFα.

B5 mAb recognizes rhTNFα in Western blots. FIG. 8 shows the results of an experiment using western blotting to demonstrate B5 binding to denatured TNFα. The images have been enhanced for clarity. In lanes A–G, binding to mouse TNFα was examined and in lanes H and I binding to human TNFα was examined. The 6F11 antibody did not bind to either TNFα species and so provides a specificity control. All the human IgM mAbs, 7T1, H5, 1A6B5F and B5 bind to mouse TNFα. Furthermore, the B5 antibody also binds to human TNFα, under these conditions. These results suggest that B5 may recognize a linear epitope of rhTNFα.

B5 mAb does not neutralize the cytotoxicity of rhTNFα. The TNF sensitive cell line WEHI 164 was used to assess the ability of B5 mAb to neutralize TNFα cytotoxicity. FIG. 9 shows that A10G10 clearly neutralizes rhTNFα in a dose dependent manner as previously demonstrated by Galloway et al (cited above). At no concentration of B5, however, was any neutralization of rhTNFα observed. The same is true for the three other human IgM anti-TNFα mAbs B6, F12 and 7T1 which were tested. These data add further support to the idea that B5 and A10G10 bind different epitopes of TNF and are consistent with the ability of B5 mAb to bind soluble rhTHFα weakly.

The B5 mAb anti-rTNFα binds to the surface of several different cell lines. Since the B5 mAb binds specifically to rTNFα, several cell lines were chosen to test whether or not the mAb would bind to their surfaces. FIG. 10 shows the results of a typical experiment using two cell lines. The EBV transformed human B lymphoblastoid cell line 8B9 and the human monocyte cell line THP-1 were stained with either B5 anti-TNFα or the 6F11 anti-Pseudomonas LPS mAbs and then fluorescent anti-human IgM F(ab)'$_2$ fragments.

The 8B9 cells were stained well with the B5 mAb whereas no significant binding to the cell surface was seen with the control 6F11 mAb. B5 staining was also observed with THP-1 cells. However, fewer cells in this population were stained and the observed staining was somewhat dimmer than that seen for the 8B9 cells. Nevertheless, nearly ⅓ of the cells in the THP-1 population expressed cell surface TNFα (csTNFα), as detected with the B5 mAb. It is unclear whether this level of staining reflects some regulation of csTNFα expression or whether it is due to clonal variation within the cell line.

The concentration dependence of B5 binding to cell surfaces was examined more closely with the THP-1 monocyte and U937 histiocyte cell lines. These cells were stained with titrated amounts of B5 antibody after incubation with either no stimulus, LPS or LPS+PMA for 3 hrs. The results are shown in FIG. 11. In all cases, B5 binding to cells was dose dependent. Interestingly, more binding was observed for both cell lines when they were preincubated with LPS or LPS+PMA. This was especially apparent for the U937 cell line. This increase is consistent with the known ability of these agents to induce TNF secretion by monocyte cell lines. Upon stimulation, B5 binding to the cells was apparent, even at several hundred nanograms/ml of antibody.

Table 2 shows the results of two experiments in which the binding of B5 anti-TNFα mAb was surveyed. Cells were stained with the indicated primary antibodies and fluorescein labeled anti-human IgM (µ-specific) secondary antibody. The percentages of cells staining positively are shown as determined on a FACSCAN instrument.

TABLE 2

Binding of the TNFα Specific B5 human IgM mAb to Various Cell Lines

| | | | % Cells Staining Positively primary antibody | | |
|---|---|---|---|---|---|
| Expt | Line | Phenotype | none | B5 | 6F11 |
| 1 | 8B9-EBV | human B lymphoblast | 1.1 | 86.9 | 4.7 |
| | 1A2-EBV | human B lymphoblast | 2.3 | 64.7 | 2.7 |
| | hpb1-EBV | human B lymphoblast | 2.0 | 96.2 | 2.3 |
| | cpb1-EBV | chimpanzee B lymphoblast | 6.6 | 76.1 | 6.2 |
| | tonsil-EBV | human B lymphoblast | 4.6 | 91.2 | 4.9 |
| | Jurkat | human T lymphoma | 0.7 | 17.9 | 1.2 |
| | LBRM33 | mouse T lymphoma | 3.1 | 72.7 | 3.8 |
| | DU4475 | human breast carcinoma | 10.2 | S2.4 | 9.8 |
| | SW1088 | human astrocytoma | 11.2 | 15.3 | 10.9 |
| | U118MG | human glioblastoma | 6.2 | 7.3 | 6.2 |
| | U373 | human glioblastoma/astrocytoma | 4.9 | 69.6 | 3.5 |
| 2 | U937 | human histiocytic lymphoma | 0.9 | 63.1 | 1.5 |
| | THP-1 | human monocyte | 1.7 | 25.2 | 2.0 |
| | 1A2-EBV | human B lymphoblast | 2.2 | 98.4 | 2.9 |
| | 8B9-EBV | human B lymphoblast | 4.7 | 98.8 | 5.4 |
| | A375 | human melanoma | 1.7 | 8.5 | 2.5 |

A variety of cell lines were tested including those of human B and T lymphocyte, breast carcinoma, astrocytoma, glioblastoma, monocyte, histiocyte, melanoma, and monoblast origin. A mouse T cell lymphoma was tested as well. Of the 15 lines tested, only the breast carcinoma U118MG showed no binding by B5. The others exhibited a range in the percentages of cells within each population which expressed csTNFα from a low of around 8% for the A375 melanoma to over 90% for EBV transformed B cells. The class matched 6F11 anti-LPS mAb failed to stain any of these cell lines. This and the negative cell line indicate that the B5 staining seen was specific and not the result of a general affinity for all cells.

Lack of Neutralizing Mouse anti-TNFα mAb Binding to cs TNFα

ELISA experiments have shown the TNF specificity of the B5 mAb and demonstrated its binding to an epitope on TNFα different from that bound by the neutralizing mouse mAb A10G10. We next examined whether or not the epitope recognized by A10G10 mAb was expressed on the surface of cells to which B5 binds.

Table 3 presents data from five experiments addressing this issue using the U937 and THP-1 cell lines. Cells were stained with the indicated primary antibodies and fluorescein labeled anti-mouse IgG (γ-specific) or anti-human IgM (µ-specific) secondary antibodies. The asterisk (*) indicates that F(ab)'$_2$ fragments of A10G10 mAb were used. The percentages of cells staining positively are shown as determined on a FACSCAN instrument. Not determined is signified by nd.

TABLE 3

Binding of Human B5 and Lack of Binding of Mouse A10G10 anti-TNFα mAbs to Cell Surface TNF on Unstimulated Monocyte and Histiocyte Cell Lines

| | | % Cells Staining Positively Primary Antibody | | | | | |
|---|---|---|---|---|---|---|---|
| Expt | Cell Line | none | A10G10 | mIgG$_1$ | none | B5 | 6F11 |
| 1 | U937 | 0.3 | 0.4 | nd | 2.9 | 15.1 | 2.7 |
| 2 | THP-1 | 0.9 | 2.6 | nd | 2.3 | 24.8 | 2.8 |

TABLE 3-continued

Binding of Human B5 and Lack of Binding of Mouse A10G10
anti-TNFα mAbs to Cell Surface TNF on
Unstimulated Monocyte and Histiocyte Cell Lines
% Cells Staining Positively
Primary Antibody

| Expt | Cell Line | none | A10G10 | mIgG$_1$ | none | B5 | 6F11 |
|---|---|---|---|---|---|---|---|
|  | U937 | 0.8 | 2.4 | nd | 2.7 | 99.1 | 2.8 |
| 3 | THP-1 | 3.1 | 2.7 | nd | 2.7 | 34.7 | 3.4 |
|  | U937 | 1.6 | 1.9 | nd | 1.6 | 35.7 | 1.8 |
| 4 | THP-1 | 2.4 | 3.1 | 1.6 | 1.7 | 17.7 | 3.4 |
|  | U937 | 2.8 | 2.9 | 2.8 | 2.2 | 20.2 | 2.7 |
| 5 | THP-1 | 4.7 | 6.0* | 6.7 | 4.6 | 56.3 | nd |
|  | U937 | 1.5 | 9.9* | 2.3 | 1.2 | 61.4 | nd |

In all five experiments the B5 mAb bound to each cell line. On the other hand, A10G10 mAb did not bind, to a significant degree, in four of the experiments. In one of the five experiments, a small amount of binding by A10G10 to the U937 cells was observed. Taken together, these data suggest that TNFα is on the surface of these cell lines, but the epitope recognized by A10G10 is only rarely available for binding by mAbs in the absence of exogenous stimulation.

LPS Induction of cell surface TNFα Expression

LPS is a commonly used agent to induce TNFα secretion by human monocytes. We incubated THP-1 and U937 cells with LPS to examine whether or not csTNFα expression can be increased. Table 4 shows the results of three experiments. Stimulation was performed by 3 or 4 hour incubation with 100 ng/ml LPS. Cells were stained with the indicated primary antibodies and fluorescein labeled anti-mouse IgG (γ-specific) or anti-human IgM (μ-specific) secondary antibodies. The asterisk (*) indicates that F(ab)'$_2$ fragments of A10G10 mAb were used. The percentages of cells staining positively are given as determined on a FACSCAN. Not determined is signified by nd.

TABLE 4

Analysis of Cell Surface Expression of TNFα After
Induction with Lipopolysaccharide
% Cells Staining Positively
Primary Antibody

| Expt | Cell Line | LPS | none | A10G10 | mIgG$_1$ | none | B5 | 6F11 |
|---|---|---|---|---|---|---|---|---|
| 1 | THP-1 | − | 3.1 | 2.7 | nd | 2.7 | 34.7 | 3.4 |
|  |  | + | 6.9 | 16.5 | nd | 3.7 | 43.8 | 3.6 |
|  | U937 | − | 1.6 | 1.9 | nd | 1.6 | 35.7 | 1.8 |
|  |  | + | 3.9 | 12.7 | nd | 1.9 | 43.5 | 2.6 |
| 2 | THP-1 | − | 2.4 | 3.1 | 1.6 | 1.7 | 17.7 | 3.4 |
|  |  | + | 3.1 | 8.3 | 2.2 | 3.0 | 29.6 | 3.2 |
|  | U937 | − | 2.8 | 2.9 | 2.8 | 2.2 | 20.2 | 2.7 |
|  |  | + | 3.6 | 11.8 | 2.4 | 2.4 | 28.4 | 3.2 |
| 3 | THP-1 | − | 4.7 | 6.0* | 6.7 | 4.6 | 56.3 | nd |
|  |  | + | 8.1 | 4.9* | 5.4 | 5.0 | 65.9 | nd |
|  | U937 | − | 1.5 | 9.9* | 2.3 | 1.2 | 61.4 | nd |
|  |  | + | 1.0 | 13.1* | 3.7 | 0.7 | 49.3 | nd |

In all three experiments, LPS increased the amount of B5 binding to THP-1 cells. This was true also for U937 cells in two of the three experiments. In contrast to noninduced cells, LPS stimulation led to the ability to be stained by the A10G10 mAb for both the THP-1 and the U937 lines. Nevertheless, the percentages of cells in either line expressing TNFα epitopes recognized by A10G10 were small, in comparison to those percentages seen with the B5 mAb.

These data suggest that csTNFα can be increased by incubation with LPS and that this increase correlates with the acquisition of TNFα epitopes recognized by neutralizing antibodies.

Influence of Factors other than LPS on csTNFα Expression

During the course of our experiments, some of our cell lines lost some spontaneous csTNFα expression. To examine the influence of fetal bovine serum (FBS) on csTNFα expression, THP-1 cells were cultivated four days in the different lots of fetal bovine sera and analyzed for cell surface TNFα expression. Table 5 shows typical results. Shown are the percentages of cells staining positively with the indicated primary and fluorescent secondary staining antibodies. The endotoxin concentrations, in Limulus amebocyte lysate units, for FBS lots 1079, 1087, 2081 and 1026 are 0.125, 0.250, 0.060 and 0.750, respectively. Analyses were performed with a FACSCAN instrument.

TABLE 5

Influence of Fetal Bovine Serum on Cell Surface
Expression of TNFα by THP-1 Cells

| | | FBS Lot # | | | |
|---|---|---|---|---|---|
| 1st Ab | 2nd Ab | 1079 | 1087 | 2081 | 1026 |
|  |  | % cells staining positively | | | |
| none | none | 0.2 | 0.3 | 0.1 | 0.2 |
| none | FL-anti-IgM | 2.2 | 3.5 | 1.6 | 2.6 |
| B5 | FL-anti-IgM | 29.5 | 15.1 | 6.8 | 14.1 |
| 6F11 | FL-anti-IgM | 6.7 | 7.1 | 4.2 | 5.2 |

The FBS lot had a large influence on csTNFα expression by THP-1 cells. The difference in expression varied by about a factor of four depending on the particular FBS batch used. Comparison of the endotoxin levels in these different lots revealed no direct correlation with csTNFα levels. These data suggest that factors other than LPS can influence expression of csTNFα.

Specificity of B5 mAb Binding to csTNFα

Table 6 presents data which confirm the specificity of B5 mAb binding to the THP-1 cells. B5 mAb at 10 ug/ml was incubated with the indicated concentrations of inhibitors prior to exposure to LPS stimulated THP-1 cells. Its binding was detected with fluorescein conjugated F(ab)'$_2$ anti-human IgM antibody. LT is recombinant human lymphotoxin, ECD55 is the recombinant extracellular TNFα binding domain of the p55 TNF receptor and A10G10 is the neutralizing mouse IgG$_1$ anti-TNFα mAb. Analyses were performed with a FACSCAN instrument.

TABLE 6

Specificity of B5 anti-TNFα mAb
binding to THP-1 Cell Surface

| | % Cells Staining Positively | | | | |
|---|---|---|---|---|---|
| | ug/ml Inhibitor | | | | |
| inhibitor | 0.0 | 0.03 | 0.30 | 3.0 | 30.0 |
| TNFα | 44.1 | 43.2 | 35.9 | 22.2 | 15.8 |
| LT | 44.1 | 39.8 | 40.0 | 40.0 | 29.7 |
| A10G10 | 44.1 | 39.6 | 40.9 | 44.4 | 41.9 |

Preincubation of the B5 IgM mAb with TNFα inhibited its subsequent cell surface binding, in a dose dependent manner, whereas preincubation with lymphotoxin did not, except for a small effect at the highest concentration. The lack of complete inhibition with the high doses of TNFα is consistent with the previously documented low affinity of this mAb for soluble TNFα. Interestingly, preincubation of B5 mAb with A10G10 and subsequent addition of both did not decrease B5 binding. These data suggest that neutralizing A10G10 does not compete for the same epitope on TNFα to which B5 mAb binds.

B5 Binds to csTNFα on Fresh Human Spleen Cells

The previous sections establish B5 binding to csTNFα on several different cell lines. To determine whether or not B5 binds to untransformed cells, experiments were performed with human splenocytes.

mAbs. Underlined values represent those which show significant increases in the percentage of positively stained cells or show greater than twice the fluorescence intensity of the appropriate control population. Analyses were performed with a FACSCAN instrument.

TABLE 7

Analysis of cell surface TNFα Expression on Fresh Human Spenocytes

% Cells Staining Positively
(median fluorescence intensity channel)

| Cells Analyzed | 1st Ab: none 2nd Ab: anti-IgM | B5 anti-IgM | 7T1 anti-IgM | H5 anti-IgM | 6F11 anti-IgM |
|---|---|---|---|---|---|
| Spleen #1: | | | | | |
| lymphocytes | 37.9(86) | 60.0(246) | 44.6(94) | 48.0(95) | 37.5(88) |
| CD3+ | 4.8(21) | 28.9(19) | 10.5(29) | 10.6(22) | 3.9(24) |
| LeuM3+ | 7.4(125) | 28.9(76) | 77.1(106) | 67.5(124) | 8.6(84) |
| Spleen #2: | | | | | |
| CD3+ | 8.8(32) | 88.3(54) | 5.5(46) | 13.7(47) | 7.1(28) |
| CD19+ | 57.5(125) | 97.5(910) | 71.2(145) | 72.2(138) | 55.7(124) |
| Leu-M3+ | 7.7(196) | 49.8(163) | 66.8(2272) | 58.9(1604) | 9.1(173) |

To analyze B cell expression of csTNFα by B5, we used unconjugated B5 IgM since direct fluoresceination or biotinylation of this antibody was very inefficient or interfered with its TNFα binding ability. Fluorescent F(ab)'$_2$ fragments of anti-human IgM antibody were used to detect B5 binding. Since many normal B cells already express sIgM as an antigen receptor, it was not always possible to detect csTNFα as an increase in the percentage of sIgM+ cells. We could, however, detect csTNFα by measuring the increase in staining intensity with the fluorescent anti-IgM when cells are incubated with the B5 mAb compared to incubation with either control 6F11 IgM mAb or no antibody at all.

FIG. 12 demonstrates this shift in fluorescence intensity seen when the B5 mAb binds to B cells. FIG. 12A shows the fluorescence histogram of cells stained with anti-IgM antibody alone. FIG. 12B shows a histogram of these same cells when first reacted with B5 mAb anti-TNFα and subsequently restained with florescent anti-IgM antibody. The most useful statistic to measure this shift is the median channel of fluorescence intensity, or simply median channel. The median channel numbers are presented in the following tables when B cells are examined.

Table 7 presents the data from two experiments using splenic biopsy material. The expression of csTNFα on monocytes, T cells and B cells was examined by two color immunofluorescence analysis using phycoerythrin conjugated anti-LeuM3, anti-CD3 and anti-CD19, respectively, in conjunction with fluorescein conjugated anti-human IgM. Human splenocytes received one day after biopsy were analyzed for expression of cell surface staining with the indicated monoclonal antibodies. Small lymphocytes were gated by forward and side scatter properties and then analyzed. T cells, B cells and monocytes were stained with phycoerythrin conjugated anti-CD3, anti-CD19 and anti-LeuM3 antibodies, respectively. Two color analyses were then performed on these populations using fluorescein labeled F(ab)'$_2$ anti-human IgM and the indicated IgM In both experiments, monocytes constituted less than 5% of the total splenocyte populations. Of these, a significant fraction in both experiments were stained with the anti-TNFα B5 mAb. On the other hand, these cells were not stained with the control 6F11 human IgM mAb. These results suggest that some splenic monocytes express csTNFα.

CD3+ T cells showed variable expression of csTNFα. While the percentages of csTNFα positive T cells varied in these experiments, the staining with the B5 mAb was much weaker than that seen for B cells and monocytes. The median fluorescence intensity for T cell csTNFα was not even twice that seen for the background controls. These results suggest that a variable proportion of splenic T cells express small amounts of csTNFα.

Analysis of B cell csTNFα expression revealed quite strong csTNFα expression. As seen in spleen Z, the percentage of IgM+ B cells increased after incubation with B5 mAb. Furthermore the staining intensity of the entire B cell population approximately tripled. No increase in staining was seen with the 6F11 control antibody, indicating the specificity of the B5 staining on B cells.

The polyreactive mAb 7T1 and H5 were included in these analyses. In addition to binding to TNFα, these antibodies react with several other antigens. Hence the specificity of their cell surface binding is unknown. We include them for comparison not only since they do bind to TNF, but also since little data on binding of polyreactive mAbs to unfixed cells is available. These antibodies do appear to react with T cells and B cells but they react with monocyte surfaces far better. In addition to significant increases in the percentages of B and T cells staining with these antibodies, the majority of monocytes in both experiments were stained.

These data suggest that the B5 anti-TNFα mAb can react with splenic lymphocytes of the B and T lineages as well as being able to recognize and bind to splenic monocytes.

B5 Binding to csTNFα on Cultured Human Spleen Cells

Spleen cells from one individual examined in Table 7 were cultivated in vitro for 3 days with various stimuli and were then analyzed for B5 mAb binding. Results are shown in Table 8. Cultivation of these cells resulted in loss of monocytes so data for Leu-M3+ cells are not presented. The cells were stained for CD3 or CD19 with phycoerythrin conjugated antibodies to allow two color analyses with fluorescein conjugated F(ab)'$_2$ anti-human IgM and the indicated human IgM mAbs. All cells were analyzed when no activator was included in culture but only large activated cells were analyzed from cultures which included activators. Underlined values represent those which show significant increases in the percentage of positively stained cells or show greater than twice the fluorescence intensity of the appropriate control population. Analyses were performed with a FACSCAN instrument.

B cells activated by either anti-IgD-dextran or *Staphylococcus aureus* Cowan Strain I (SAC), both potent B cell mitogens, demonstrated binding by B5 anti-TNFα mAb. The higher B5 staining fluorescence intensity seen after SAC induction suggests a higher B cell surface level of TNFα expression than seen on anti-IgD activated B cells, or B cells cultured in medium alone. These data suggest that both activated human B cells and T cells express csTNFαepitopes recognized by the B5 mAb.

Binding of B5 mAb to Human and Chimpanzee Peripheral Blood Lymphocytes

To extend the finding of human splenic lymphocyte expression of csTNFα, peripheral blood lymphocytes of human and chimpanzee origin were examined. Table 9 shows the results obtained with blood from two chimpanzees and one human. The chimpanzee blood was received

TABLE 8

Analysis of Cell Surface TNFα Expression by Cultured Human Splenic Lymphocytes
% Cells Staining Positively
(median fluorescence intensity channel)

| Activator | Cell | 1st AB –<br>2nd Ab – | –<br>+ | B5<br>+ | 7T1<br>+ | H5<br>+ | 6F11<br>+μ |
|---|---|---|---|---|---|---|---|
| none | CD3+ | 0.1(154) | 9.3(48) | 42.2(17) | 11.8(34) | 16.6(25) | 10.0(57) |
|  | CD19+ | 1.0(22) | 85.1(54) | 99.4(294) | 91.8(56) | 96.1(96) | 86.8(52) |
| anti-δ-Dex plus IL-2 | CD19+ | 4.0(76) | 96.0(58) | 100.0(272) | 99.5(82) | 99.9(224) | 97.4(57) |
| SEB | CD3+ | 9.1(110) | 24.4(102) | 66.4(84) | 44.8(82) | 53.8(87) | 26.1(106) |
| SAC | CD19+ | 3.4(42) | 58.9(60) | 100.0(452) | 84.1(93) | 94.3(183) | 65.6(62) |

The cells cultured in medium were 55% CD19+ (B cells) and 22% CD3+ (T Cells). Of the CD19+ cells, 85% were sIgM+ with a median channel intensity of 54. Staining with the B5 mAb increased this intensity to median channel 294—nearly six fold higher. This increase was not seen with the polyreactive or control IgM mAbs. Increases in percentages of CD3+ T cells which bound B5 mAb were also seen, although the intensity of staining was low. Despite the fact that anti-IgM alone revealed some T cell staining, addition of 6F11 to these T cells did not result in increased anti-IgM staining, showing the specificity of B5 staining and suggesting the B5 mAb is not binding to the IgM receptors expressed on activated T cells. These receptors are presumably already occupied and account for the background staining observed with the anti-IgM secondary antibody.

Stimulation with the superantigen Staphylococcal Enterotoxin B (SEB), which activates both T and B cells, resulted in about 24% of the T cells binding the secondary anti-human IgM antibody. However, about 66% of the SEB activated T cells bound B5 anti-TNFα mAb. No increase in sIgM+ T cells was seen with the 6F11 control mAb. These data indicate induction of csTNFα expression when T cells are activated.

one day after it was drawn whereas the human blood was fresh. The delay in receipt of the blood appeared to result in loss of monocytes from the chimpanzee blood. Peripheral blood mononuclear cells were prepared by separation on Ficoll and stained with PE derivatized anti-CD3, CD19 or LeuM3. For the chimpanzees 171 and 203, less than 2% and 0.6% of cells were LeuM3+, respectively. Some 20.2% of the human cells were LeuM3+. T cells comprised 62% and 54% of the chimpanzee lymphocytes and 68% of the human lymphocytes. B cell percentages were 2.8 and 5.4 for the chimpanzees and 16.4% for the human. Cells were incubated with the indicated IgM primary antibodies and subsequently stained with the fluorescein conjugated F(ab)'$_2$ anti-human IgM reagent. Analyses were performed with a FACSCAN instrument. Underlined values represent those which show significant increases in the percentage of positively stained cells or show greater than twice the fluorescence intensity of the appropriate control population.

TABLE 9

Analysis of Chimpanzee and Human Peripheral Blood
T Cell and B Cell Expression of Cell Surface TNFα
positive cells (median channel intensity)

| primary Ab<br>anti-IgM | –<br>– | –<br>+ | 6F11<br>+ | B5<br>+ | 7T1<br>+ | H5<br>+ |
|---|---|---|---|---|---|---|
| Chimp 171 |  |  |  |  |  |  |
| CD 3+ | 0.1(25) | 14.4(40) | 14.8(41) | 31.9(23) | 18.2(39) | 21.5(28) |
| CD19+ | 0.4(10 | 98.6(196) | 98.4(196) | 99.6(704) | 98.9(230) | 99.6(312) |

TABLE 9-continued

Analysis of Chimpanzee and Human Peripheral Blood
T Cell and B Cell Expression of Cell Surface TNFα
positive cells (median channel intensity)

| primary Ab | – | – | 6F11 | B5 | 7T1 | H5 |
|---|---|---|---|---|---|---|
| anti-IgM | – | + | + | + | + | + |
| Chimp 203 | | | | | | |
| CD3+ | 0.0(13) | 30.9(26) | 32.1(27) | 53.6(27) | 31.2(25) | 42.0(24) |
| CD19+ | 0.6(13) | 92.3(70) | 90.1(79) | 99.4(491) | 95.1(101) | 98.0(196) |
| Human | | | | | | |
| CD3+ | 0.6(17) | 1.7(24) | 3.3(22) | 17.1(15) | 2.8(19) | 4.5(16) |
| CD19+ | 1.3(37) | 83.5(75) | 84.6(70) | 99.4(316) | 91.5(78) | 96.1(96) |
| LeuM3+ | 1.2(26) | 5.6(9) | 4.2(84) | 4.8(106) | 35.3(74) | 30.4(82) |

In contrast to the previous results with human spleen, the fresh peripheral human monocytes did not express csTNFα as seen by the B5 mAb. A significant fraction of these cells did, however, bind the polyreactive mAbs 7T1 and H5.

The fresh human T cells did not express surface IgM whereas the chimpanzee T cells drawn one day previously did. T cells from both species, however, expressed modest amounts of csTNFα detected by the B5 mAb. This anti-TNFα staining was very weak, however, and suggests only low levels of csTNFα were present. T cells from neither species were recognized by polyreactive 7T1 or H5.

In contrast to the T cells, peripheral blood B cells from both chimpanzees and the human displayed high levels of csTNFα seen by B5 mAb. This expression was much more intense than that seen with the T cells. These results suggest that normal human peripheral blood monocytes do not express csTNFα whereas some T lymphocytes and most B lymphocytes from both species do express this cell surface cytokine.

B5 anti-TNFα mAb inhibits LPS induced secretion of TNFα by THP-1 Cells

To examine whether or not the binding of B5 mAb to csTNFα had any functional significance, we stimulated the THP-1 human monocyte cell line with LPS in the presence of B5 or other human IgM mAbs. We assayed secretion of biologically active TNFα by measuring cytotoxic activity of the supernatants on the TNFα sensitive WEHI 164 cell line. The results of two of four such experiments are given in Table 10. THP-1 cells were stimulated for 4 hours with 100 ng/ml E. coli LPS in the presence of 40 ug/ml of the indicated TNF non-neutralizing human IgM mAbs. Supernatants from these incubations were then tested for cytotoxicity against the TNFα sensitive WEHI 164 cell line. All supernatant cytotoxicity was concentration dependent and was neutralized by A10G10 anti-TNFα mAb, indicating cytotoxicity was due to TNFα. Concentrations of secreted TNFα were determined by comparison to a standard curve.

TABLE 10

Inhibition of LPS Induced TNFα Secretion by B5 mAb

| Expt | mAb | ug/ml | pg/ml TNFα | % inhibition |
|---|---|---|---|---|
| 1 | none | 0 | 1003 | 0 |
| | 6F11 | 40 | 990 | 1 |
| | 7T1 | 40 | 976 | 3 |
| | B5 | 40 | 102 | 90 |
| | " | 20 | 409 | 59 |
| | " | 10 | 812 | 19 |
| | " | 5 | 962 | 4 |
| 2 | none | 0 | 2057 | 0 |

TABLE 10-continued

Inhibition of LPS Induced TNFα Secretion by B5 mAb

| Expt | mAb | ug/ml | pg/ml TNFα | % inhibition |
|---|---|---|---|---|
| | 6F11 | 40 | 1992 | 3 |
| | B5 | 40 | 143 | 93 |
| | " | 20 | 783 | 62 |
| | " | 10 | 1271 | 38 |
| | " | 5 | 2276 | –10 |

Stimulated THP-1 cells did secrete active TNFα and all of this cytotoxic activity was inhibited by including A10G10 in the cytotoxicity assay (data not shown). Previous experiments including B5 mAb in the cytotoxicity assay have shown that B5 does not neutralize TNFα (FIG. 9). Table 10 shows that coculture of the THP-1 cells with B5 mAb inhibits LPS induced TNFα secretion. These data suggest that B5 mAb interaction with csTNFα can inhibit LPS induced TNF secretion.

An additional feature of the antibodies of this disclosure is that they can be used to mediate inhibition of mitogen-induced proliferation of human lymphoid cells as shown in Table 11 below.

TABLE 11

B5 mAb-Mediated Inhibition of Mitogen-Induced
Proliferation of Human Lymphoid Cells

| | cpm × 10⁻³ Antibody Added to Culture | | |
|---|---|---|---|
| Mitogen | None | B5 | 6F11 |
| none | 200 | 100 | 200 |
| anti-IgD-dextran + IL-2 | 6150 | 2550 | 5450 |
| Pansorbin | 4650 | 2450 | 4450 |
| EBV | 1300 | 600 | 900 |

Human splenocytes were cultured for 3 days with the indicated mitogens and antibodies. 3HTdR was added on the final day for 6 hours, then cells were harvested and thymidine incorporation was assessed.

Usefulness of the Invention

The mAbs of this Application have several useful features.

First, the human monoclonal anti-TNF antibodies of this disclosure could be used to detect and/or measure TNF in vitro using conventional immunoassay techniques. For example, they could be used is a diagnostic manner to assess expression of cell surface TNF on human and murine cells, and perhaps cells from other species.

Second, by binding to cells expressing surface TNF, the antibody may initiate killing of these cells via complement fixation. This might prove useful for depleting cells expressing surface TNF. For example, cells from a patient might be removed, treated with the antibody and complement, or a similar reagent leading to cytotoxicity of cells bound by the antibody, and the remaining cells might be reintroduced back into the donor. This might be useful in depleting patients of peripheral B cell leukemia cells, or other leukemic cells expressing surface TNF.

Third, the antibody might be introduced into patients as a therapeutic agent to help kill or remove cells expressing surface TNF. We have shown many activated cells, including some carcinoma cell lines express surface TNF. These types of cells, as well as others expressing surface TNF, could serve as appropriate targets for treatment by this antibody invention.

Fourth, the antibody might be introduced into patients where TNF production contributes to the disease process or state. The aim here would be to inhibit TNF production. Since we have shown that binding of the antibody can inhibit TNF secretion by some cells, this avenue of therapy may be beneficial.

Fifth, the antibody might be introduced into patients to slow or inhibit the growth of cells expressing surface TNF. We have shown that mitogen activated human cells can express surface TNF that is bound by the B5 antibody. (See Table 11.) Again, a specific application might be in cancer or leukemia therapy.

A primary advantage of this invention is that it comprises a human anti-TNF antibody and, as such, it is expected to be far less immunogenic than antibody from any other species. The properties which distinguish the invention from any putative and ill-defined natural anti-TNF antibody are its specificity and binding capacity. Unlike the B5mAb invention described in this disclosure, no other human antibodies in the literature have been proven to be TNF-specific.

DISCUSSION

To our knowledge, this is the first report of a monoclonal human autoantibody specific for human and mouse TNFα. It is unclear whether or not the CMV seropositive donor origin of B5 mAb is significant. The antibody is clearly different from the mouse mAbs we have generated to TNFα, all of which are neutralizing, as shown previously by Galloway et al (cited above).

Three lines of evidence suggest that B5 mAb recognizes an epitope different from those recognized by the mouse mAbs described. First, there is no competition between the human and mouse mAbs for binding to plates coated with TNF. Second, TNF bound by the human mAb can be recognized by the mouse mAbs, and vice versa. Finally, B5 mAb does not neutralize rhTNFα whereas the mouse mAbs do. One might argue that TNFα is a trimer and, as such, TNFα bound to neutralizing mouse mAbs attached to plates can still present an identical epitope to be recognized by mAb B5. The lack of competition between the mouse mAbs and mAb B5 for plate bound TNFα is a strong argument against this possibility. The competition data in combination with the lack of neutralizing activity of B5 mAb support the interpretation of distinct epitope recognition by the mouse and human mAbs. The biological effects of TNFα, especially its ability to promote Ig secretion, may preclude the generation of a high affinity neutralizing human anti-TNFα autoantibody by the techniques used. This ability may also explain the different epitope specificities of B5 mAb and the three neutralizing mouse mAbs.

The base of the bell shaped trimeric TNFα molecule, which contains the amino terminus apposed to the carboxy terminus, is the region of the molecule which binds to TNF receptors (M. J. Eck et al "The Structure of Tumor Necrosis Factor-α at 2.6Å Resolution, Implications for Receptor Binding." J. Biol. Chem. 264:17595–605, 1989; and A. Corti et al "Antigenic Regions of Tumor Necrosis Factor Alpha and Their Topographic Relationships with Structural/ Functional Domains." Molec. Immunol. 29:471–9, 1992). Since the mouse mAbs used in this report neutralize TNFα, and have been found to block binding of TNFα to its receptors, it is likely that an epitope in the base of the trimer is recognized by these antibodies. From the data presented in this report, one might speculate that the B5 mAb sees a region of the TNFα molecule closer to the "top" of the trimer.

The weak binding of B5 mAb to soluble TNFα is consistent with a low binding constant of the mAb for the ligand. Nevertheless, the valency of this IgM mAb can outweigh this shortcoming so that B5 can bind to solid phase TNFα as well as, or better than, the high affinity neutralizing mouse anti-TNFα mAbs tested. Apparently, multipoint binding allows the mAb B5 to adhere strongly to TNFα when a sufficient antigen density is available.

Although B5 appears to bind with low affinity, we show that it binds specifically to TNFα and fails to bind to any of the other antigens tested. This contrasts with the observed binding of two other control polyreactive mAbs. Hence, B5 appears to be monospecific and is not polyreactive. B5 seems to bind specifically to an epitope, most likely a linear epitope, shared by mouse and human TNFα. These properties classify B5 as an autoantibody and distinguish it from other mAbs so far described.

The human B5 autoantibody binds to surface TNFα on a broad range of human cell lines and lymphoid cells. It is not surprising that it recognizes chimpanzee TNFα as there is no difference in the amino acid sequences of TNFα from chimpanzee and human. We have also shown that B5 recognizes mouse TNFα which is about 80% identical to human TNFα (D. Pennica et al "Cloning and expression in *Escherichia coli* of the cDNA for Murine Tumor Necrosis Factor", Proc. Natl. Acad. Sci. USA 82:6060–4, 1985). Hence it is not surprising that B5 recognizes mouse csTNFα.

Others have certainly described TNF production by human B cells (M. Jäätelä, "Biology of Disease. Biologic Activities and Mechanisms of Action of Tumor Necrosis Factor-a/Cachectin", Lab. Invest. 64:724–42, 1991; and Smeland et al "Interleukin 4 Induces Selective Production of Interleukin 6 from Normal Human B Lymphocytes", J. Exp. Med. 170:1463–68, 1989), T cells (S. -S. J. Sung et al "Production of Tumor Necrosis Factor/Cachectin by Human T Cell Lines and Peripheral Blood T Lymphocytes Stimulated by Phorbol Myristate Acetate and Anti-CD3 Antibody", J. Exp. Med. 167:937-, 1988), monocytes (Beutler et al "The Biology of Cachectin TNF-α: Primary Mediator of the Host Response", Ann. Rev. Immunol. 7:625–55, 1989), B cell lines (S. -S. J. Sung et al "Production of Tumor Necrosis Factor/Cachetin by Human T Cell Lines and Peripheral Blood T Lymphocytes Stimulated by Phorbol Myristate Acetate and Anti-CD3 Antibody", J. Exp. Med. 167:937-, 1988; and G. J. Jochems et al "Heterogeneity in Both Cytokine Production and Responsiveness of a Panel of Monoclonal Human Epstein-Barr Virus-Transformed B-Cell Lines", Hum. Antibod. Hybridomas 2:57–64, 1991), astrocytes (A. P. Lieberman et al "Production of Tumor necrosis Factor and other Cytokines by Astrocytes Stimulated with Lipopolysaccharide or a Neurotropic Virus", Proc. Natl. Acad. Sci. USA, 86:6348–52, 1989; and I. Y. Chung et al "Tumor Necrosis Factor Alpha Production by Astrocytes: Induction by Lipopolysaccharide, IFN-gamma, and IL-1 beta", J. Immunol. 144:2999–3007, 1990; and K. Selmaj et al "Identification of Lymphotoxin and Tumor necrosis Factor in Multiple Sclerosis Lesions", J. Clin. Invest. 87:949–54, 1991) as well as some TNF resistant cell lines (B. Y. Rubin et al "Nonhematopoietic Cells Selected for Resistance to Tumor Necrosis Factor Produce Tumor Necrosis Factor", J. Exp. Med. 164:1350–5, 1986). We extend these findings to include at least one metastatic breast carcinoma, DU4475, a melanoma, A375, and the U373 astrocytoma/glioblastoma. We also demonstrate csTNFα expression on human splenic lymphoid cells. This is somewhat surprising since previous demonstration of csTNFα by others tended to employ activated cells.

Although we examined small lymphocytes, as determined by light scatter properties, it is possible many of these cells were partially activated or at a stage of differentiation where they could express this cell surface molecule. The smaller percentages of T lymphocytes and monocytes from human peripheral blood expressing csTNFα is consistent with the resting phenotype of these cells. In any case, the breadth of csTNFα expression suggests it has an important role in the surface of many cells.

Others have shown that TNFα can exist as both an integral transmembrane protein and as a mature protein bound to its receptor on cell surfaces (B. Luettig et al "Evidence for the Existence of Two Forms of Membrane Tumor Necrosis Factor: an Integral Protein and a Molecule Attached to its Receptor", J. Immunol. 143:4034–38, 1989). Several observations suggest that the B5 mAb recognizes the integral transmembrane protein. B5 binding was increased when cells were activated with LPS or PMA. Both agents, but especially PMA, down regulate TNF receptor expression on a variety of cell types (A. H. Ding et al "Macrophages Rapidly Internalize their Tumor Necrosis Factor Receptors in Response to Bacterial Lipopolysaccharide", J. Biol. Chem. 264:3924–9, 1989; and B. A. Aggarwal et al "Effect of Phorbol Esters on Down-Regulation and Redistribution of Cell Surface Receptors for Tumor Necrosis Factor α", J. Biol. Chem. 262:16450–5, 1987).

B5 binds to unstimulated cell lines whereas cell lines normally need to be induced to secrete TNF. Hence, unstimulated cell lines would be expected to display little receptor bound TNF. We showed that B5 binding to cell surfaces was inhibited by preincubation with TNFα, but not A10G10 anti-TNFα mAb. This demonstrates the specificity of the B5 antibody.

TNFβ binds to the same receptors as TNFα and so might compete off some receptor bound TNFα on cell surfaces. The data in Table 6 with high doses of TNFβ suggest that this did occur, and was detected by a decrease in B5 staining. For these reasons, it is likely that B5 recognizes the 26 kd transmembrane form of TNFα and possibly receptor bound TNF.

One puzzling result of these studies is that B5 mAb binds to csTNFα in many situations in which A10G10 binding is either absent or less than that seen with B5. It is clear that these two antibodies see non-overlapping epitopes. Since A10G10 neutralizes TNFα cytotoxicity and prevents TNFα binding to its receptor, this mouse mAb probably binds to TNFα near the receptor binding domain.

Others have shown that mAbs which bind the amino terminal 15 or so amino acids block TNFα cytotoxicity (S. H. Socher et al "Antibodies Against Amino Acids 1–15 of Tumor Necrosis Factor Block Its Binding to Cell-Surface Receptor" Proc. Natl. Acad. Sci. USA 84:8829–33, 1987). Hence, it is possible that A10G10 binds to some of the N-terminal amino acids which are most membrane proximal on the transmembrane form of TNFα. This region may not be accessible to A10G10 for binding, although the TNF molecule itself is present and can be recognized by B5 mAb.

Western blotting experiments suggest that A10G10 does not recognize TNFα monomers and probably recognizes a conformational epitope (data not shown). If transmembrane TNFα is primarily monomeric, epitopes recognized by A10G10 may not be present. Additional experiments may help to decide between these and other possibilities.

Interestingly, we did observe A10G10 cell surface binding when cells were activated with LPS. This induction causes secretion of the biologically active TNFα trimer which can then bind to remaining TNF receptors. Since trimeric TNFα is multivalent, it may bind to some receptors in a way which allows one or even two remaining receptor binding domains to remain free. It may be this form of csTNFα which is recognized by A10G10. Indeed, others have shown that incubating unactivated paraformaldehyde-fixed human monocytes with TNFα results in TNFα binding its receptors and renders these monocytes cytotoxic. Furthermore, this cytotoxicity is abolished by neutralizing anti-TNF antibodies (A Nii et al "The Incubation of Human Blood Monocytes with Tumor Necrosis Factor-Alpha Leads to Lysis of Tumor Necrosis Factor-Sensitive but not Resistant Tumor Cells", Lymphokine Res. 9:113–24, 1990).

One model which explains much of the data is that transmembrane TNFα monomers are recognized by B5 mAb. We have shown soluble monomer recognition by B5. Cell surface TNFα monomers might exhibit an overall conformation different from that of trimeric TNF. They may still expose TNF receptor binding domains and so be capable of mediating cytotoxicity through cell contact. Cells expressing many monomers could thus cause TNF receptor cross-linking on target cells. An activation signal could cause polymerization of TNF monomers in the cell membrane, leading to a conformational change which, in turn, might expose a proteolytic cleavage site leading to release of mature, biologically active trimeric TNFα. Release could be followed by interaction with TNF receptors and allow A10G10 binding, as suggested above. B5 apparently binds to membrane distal TNF domains and, by so doing, may interfere with either csTNFα polymerization, a subsequent conformational change, or both. B5 probably does not bind to the proteolytic cleavage site since it does bind to the mature trimeric molecule. This model would explain the cell surface staining results and also explain the observed inhibition of TNF secretion after LPS activation of THP-1 cells. It should be noted that this model allows for a role of the cytoplasmic domain in csTNFα polymerization. This is only a working model and, as such, is admittedly hypothetical.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes coming within the meaning and range of equivalency of the claims are therefore intended to be embraced therein.

We claim:

1. A composition comprising human monoclonal antibodies that bind specifically to human tumor necrosis factor alpha.

2. The composition of claim 1 wherein the antibodies comprise antibodies of the IgM type.

3. The composition of claim 1 wherein the antibodies comprise antibodies of the IgG type.

4. The composition of claim 1 wherein the antibodies also bind to mouse tumor necrosis factor alpha.

5. The composition of claim 1 wherein the antibodies can bind to non-neutralizing epitopes of tumor necrosis factor alpha.

6. The composition of claim 1 wherein the antibodies are specific for tumor necrosis factor alpha.

7. The composition of claim 1 wherein the antibodies bind to tumor necrosis factor alpha on human cell surfaces.

8. The composition of claim 1 wherein the antibodies inhibit secretion of tumor necrosis factor alpha.

9. The composition of claim 1 wherein the antibody is expressed from the cell line designated F78-1A10-B5 having A.T.C.C. Recession No. 11306.

10. A human monoclonal antibody preparation characterized by binding specifically to human TNF alpha, and having a titer comparable to three high affinity neutralizing mouse monoclonal antibodies when tested by ELISA.

11. The antibody preparation of claim 10 having the further characteristic of binding to cell surface TNF alpha on cells selected from the group consisting of human T cells, B cells, monocytes and lymphoid and monocyte lineage cell lines of human origin.

12. The antibody preparation of claim 10 having the further characteristic of inhibiting LPS induced TNF alpha secretion by human monocyte-like cells.

* * * * *

(12) EX PARTE REEXAMINATION CERTIFICATE (8643rd)

United States Patent
Boyle et al.

(10) Number: US 5,654,407 C1
(45) Certificate Issued: Nov. 1, 2011

(54) HUMAN ANTI-TNF ANTIBODIES

(75) Inventors: Petra Boyle, Pinole, CA (US); Gayle D. Wetzel, Martinez, CA (US); Kenneth J. Lembach, Danville, CA (US)

(73) Assignee: Bayer Healthcare LLC, Tarrytown, NY (US)

Reexamination Request:
No. 90/010,725, Oct. 30, 2009
No. 90/011,007, May 20, 2010

Reexamination Certificate for:
Patent No.: 5,654,407
Issued: Aug. 5, 1997
Appl. No.: 08/435,246
Filed: May 5, 1995

Related U.S. Application Data

(63) Continuation of application No. 08/145,060, filed on Oct. 29, 1993, now abandoned, which is a continuation-in-part of application No. 08/026,957, filed on Mar. 5, 1993, now abandoned.

(51) Int. Cl.
*A61K 38/00* (2006.01)
*C07K 16/24* (2006.01)
*C07K 16/18* (2006.01)

(52) U.S. Cl. ............ 530/388.15; 530/388.23; 530/388.24; 424/142.1; 424/145.1; 424/158.1; 435/335

(58) Field of Classification Search .............. None
See application file for complete search history.

(56) References Cited

To view the complete listing of prior art documents cited during the proceedings for Reexamination Control Numbers 90/010,725 and 90/011,007, please refer to the USPTO's public Patent Application Information Retrieval (PAIR) system under the Display References tab.

*Primary Examiner*—Padmashri Ponnaluri

(57) ABSTRACT

Human monoclonal antibodies (mAbs) which bind to human TNFα are disclosed. Autoantibodies of both the IgM and IgG isotypes are disclosed. A preferred human monoclonal antibody is known as B5 (F78-1A10-B5 mAb) and it binds to recombinant human TNFα (rhTNFα) in ELISA format with a titer comparable to three high affinity neutralizing mouse mAbs. It also binds to cell surface TNFα and prevents TNFα secretion by human monocyte cell lines.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-8 are cancelled.

Claims 9-12 were not reexamined.

\* \* \* \* \*